(12) United States Patent
Clark et al.

(10) Patent No.: US 12,416,574 B2
(45) Date of Patent: Sep. 16, 2025

(54) MEASUREMENT METHOD, MEASUREMENT DEVICE, AND NONTRANSITORY COMPUTER-READABLE MEDIUM

(71) Applicant: NEC Corporation, Tokyo (JP)

(72) Inventors: John Kenji Clark, Tokyo (JP); Shigeru Nakamura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 142 days.

(21) Appl. No.: 18/288,337

(22) PCT Filed: Jan. 18, 2022

(86) PCT No.: PCT/JP2022/001647
§ 371 (c)(1),
(2) Date: Oct. 25, 2023

(87) PCT Pub. No.: WO2022/234694
PCT Pub. Date: Nov. 10, 2022

(65) Prior Publication Data
US 2024/0241047 A1    Jul. 18, 2024

(30) Foreign Application Priority Data

May 7, 2021    (JP) ................................ 2021-079320

(51) Int. Cl.
*G01N 21/47* (2006.01)
*G01N 21/17* (2006.01)

(52) U.S. Cl.
CPC ..... *G01N 21/47* (2013.01); *G01N 2021/1757* (2013.01); *G01N 2021/1787* (2013.01); *G01N 2021/4735* (2013.01)

(58) Field of Classification Search
CPC ........ G01N 2021/1787; G01B 9/02091; A61B 3/102
See application file for complete search history.

(56) References Cited

U.S. PATENT DOCUMENTS

2019/0117076 A1*  4/2019  Fan ...................... A61B 5/0088
2019/0145754 A1   5/2019  Liu et al.

FOREIGN PATENT DOCUMENTS

JP    2016-057318 A    4/2016
JP    2019-518936 A    7/2019

OTHER PUBLICATIONS

International Search Report for PCT Application No. PCT/JP2022/001647, mailed on Apr. 12, 2022.

* cited by examiner

*Primary Examiner* — Thanh Luu
(74) *Attorney, Agent, or Firm* — Sughrue Mion, PLLC

(57) ABSTRACT

A measurement method according to an example embodiment executed by a computer includes: selecting one of a plurality of sample wavelengths as a wavelength of output light of a semiconductor wavelength-tunable laser, and controlling output of the output light in such a way that the selected one sample wavelength discretely and sequentially changes with time; acquiring, for each of the plurality of sample wavelengths, an electrical signal obtained by detecting and converting interference light obtained by combining and interfering scattered light obtained by irradiating a sample with measurement light, and reference light for the measurement light and the reference light obtained by splitting the output light; and deriving a scattering profile of the sample by performing compressed sensing on the electrical signal obtained for each of the plurality of sample wavelengths.

9 Claims, 24 Drawing Sheets

MEASUREMENT METHOD, MEASUREMENT DEVICE, AND NONTRANSITORY COMPUTER-READABLE MEDIUM

This application is a National Stage Entry of PCT/JP2022/001647 filed on Jan. 18, 2022, which claims priority from JP Patent Application 2021-079320 filed on May 7, 2021, the contents of all of which are incorporated herein by reference, in their entirety.

TECHNICAL FIELD

The present disclosure relates to a measurement method, a measurement device, and a non-transitory computer-readable medium.

BACKGROUND ART

In recent years, a technology of optical coherence tomography (OCT) for generating tomographic data of a sample by using interference light obtained by outputting measurement light to the sample and reflecting the measurement light, and combining the reflected light and reference light has been used.

For example, Patent Literature 1 discloses a technology of scanning a target object with signal light while alternately changing a phase difference between the signal light and reference light to two predetermined phase differences, and performing scanning at an oversampling ratio.

CITATION LIST

Patent Literature

Patent Literature 1: Japanese Unexamined Patent Application Publication No. 2016-057318

SUMMARY OF INVENTION

Technical Problem

An object of the disclosure is to improve the technology disclosed in Patent Literature 1.

Solution to Problem

A measurement method according to one aspect of the present example embodiment executed by a computer includes: selecting one of a plurality of sample wavelengths as a wavelength of output light of a semiconductor wavelength-tunable laser, and controlling output of the output light in such a way that the selected one sample wavelength discretely and sequentially changes with time; acquiring, for each of the plurality of sample wavelengths, an electrical signal obtained by detecting and converting interference light obtained by combining and interfering scattered light obtained by irradiating a sample with measurement light, and reference light for the measurement light and the reference light obtained by splitting the output light; and deriving a scattering profile of the sample by performing compressed sensing on the electrical signal obtained for each of the plurality of sample wavelengths. Here, parameters related to the plurality of sample wavelengths satisfy the following Formula (1).

[Mathematical Formula 1]

$$\max_{z=z_0, z_1, \ldots z_n} \hat{f}_{samp}(z) \leq \frac{m}{2h-1} \quad (1)$$

In Formula (1),

[Mathematical Formula 2]

$$\hat{f}_{samp}(z) \quad (2)$$

is a Fourier transform of a sampling mask related to the plurality of sample wavelengths, z is a specific depth at which a depth profile is extracted, m is the number of plurality of sample wavelengths, and h is the number of non-zero elements in a vector of a scattering intensity in a depth range for the scattering profile.

A measurement device according to one aspect of the present example embodiment includes: a wavelength-tunable light source configured to output output light of a semiconductor wavelength-tunable laser in such a way that a wavelength discretely changes with time; an interferometer configured to split the output light into measurement light and reference light and generate interference light obtained by combining and interfering scattered light obtained by irradiating a sample with the measurement light, and the reference light; a photodetector configured to detect the interference light and converts the interference light into an electrical signal; and a hardware controller configured to select one of a plurality of sample wavelengths as the wavelength of the output light, perform setting in such a way that the selected one sample wavelength sequentially changes with time, and derive a scattering profile of the sample by performing compressed sensing on the electrical signal obtained for each of the plurality of sample wavelengths. Here, parameters related to the plurality of sample wavelengths satisfy the following Formula (3).

[Mathematical Formula 3]

$$\max_{z=z_0, z_1, \ldots z_n} \hat{f}_{samp}(z) \leq \frac{m}{2h-1} \quad (3)$$

In Formula (3),

[Mathematical Formula 4]

$$\hat{f}_{samp}(z) \quad (4)$$

is a Fourier transform of a sampling mask related to the plurality of sample wavelengths, z is a specific depth at which a depth profile is extracted, m is the number of plurality of sample wavelengths, and h is the number of non-zero elements in a vector of a scattering intensity in a depth range for the scattering profile.

A program according to one aspect of the present example embodiment causes a computer to execute: selecting one of a plurality of sample wavelengths as a wavelength of output light of a semiconductor wavelength-tunable laser, and controlling output of the output light in such a way that the selected one sample wavelength discretely and sequentially changes with time; acquiring, for each of the plurality of sample wavelengths, an electrical signal obtained by detecting and converting interference light obtained by combining and interfering scattered light obtained by irradiating a sample with measurement light, and reference light for the measurement light and the reference light obtained by splitting the output light; and deriving a scattering profile of the sample by performing compressed sensing on the electrical signal obtained for each of the plurality of sample wavelengths. Here, parameters related to the plurality of sample wavelengths satisfy the following Formula (5).

[Mathematical Formula 5]

$$\max_{z=z_0, z_1, \dots z_n} \hat{f}_{samp}(z) \le \frac{m}{2h-1} \quad (5)$$

In Formula (5),

[Mathematical Formula 6]

$$\hat{f}_{samp}(z) \quad (6)$$

is a Fourier transform of a sampling mask related to the plurality of sample wavelengths, z is a specific depth at which a depth profile is extracted, m is the number of plurality of sample wavelengths, and h is the number of non-zero elements in a vector of a scattering intensity in a depth range for the scattering profile.

EXAMPLE EMBODIMENT

Related Art

Figure 1:
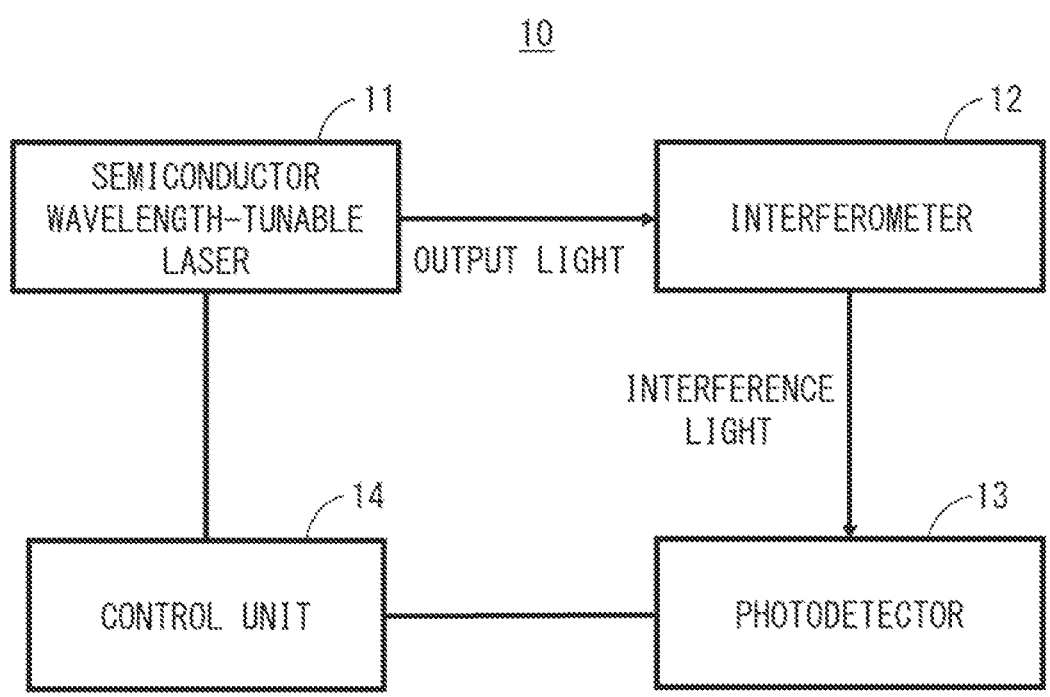
FIG. 1 is a block diagram illustrating an example of a measurement device according to a first example embodiment.

First, the related art of the disclosure will be described. OCT is a technology for acquiring a 3D tomographic image of a subsurface structure of a sample based on an interference pattern generated by backscattered light from the sample and reference light. The OCT is applied to obtain high-resolution tomographic image information in various fields such as ophthalmology, dentistry, and non-destructive inspection.

In the OCT, beam light from a light source is generally split into a reference light beam and a sample light beam. The sample light beam is then radiated to the sample, and sample light (backscattered light) backscattered from the sample interferes with the reference light beam to generate interference light. A detection device detects the interference light. From the interference pattern generated by the interference of the backscattered light with the reference light beam, a scattering profile of the sample in an axial direction (propagation direction) of the sample light beam, known as A-scan, is extracted. The exact means for extracting the A-scan depends on the type of the OCT performed. The sample light beam is scanned laterally across the sample to build a 3D image of the scattering profile of the sample.

There are two main types of OCT: time domain OCT (TD-OCT; time domain optical coherence tomography) and Fourier domain OCT (FD-OCT; Fourier domain optical coherence tomography), with different operating principles.

In the TD-OCT, a light source having a short coherence length is used, and an optical path length of the reference light beam changes depending on time. Interference between the backscattered light and the reference light occurs in a case where the two lights have the same optical path length. Thus, the A-scan scattering profile is extracted from an envelope of an interference signal.

On the other hand, in the FD-OCT, a broadband or variable wavelength light source is used, and the interference signal over a wavelength range is measured. The A-scan is extracted from the interference signal by performing the inverse Fourier transform of the interference signal in a wavenumber domain.

The FD-OCT is subdivided into spectral domain OCT (SD-OCT; spectral domain optical coherence tomography) and SS-OCT based on the types of the light source and the detection device used. In the SD-OCT, a broadband light source is used, and a spectrum-resolved interference signal is obtained by using an optical spectrometer. In contrast, in many types of SS-OCT (Swept-Source Optical Coherence Tomography), a swept-source laser is used as the light source, and a photodetector is used to detect an intensity of the interference signal. By changing the wavelength of the light source over time and measuring the intensity of the interference signal while changing the wavelength of the light source, the spectrum-resolved interference signal is obtained. The swept-source laser is different from a semiconductor wavelength-tunable laser to be described later in that a wavelength sweep is performed continuously rather than discretely. In addition, the swept-source laser has a shorter coherence length of output light and a wider band than the semiconductor wavelength-tunable laser.

In an actual implementation of an SS-OCT system, the A-scan is obtained by sampling the interference signal at a discrete set of wavelengths and applying the inverse discrete Fourier transform to the spectrum-resolved interference signal in the wavenumber domain. Here, the value of a wavenumber at a predetermined wavelength is simply the reciprocal of the wavelength. In order for the inverse Fourier transform extracted using the inverse discrete Fourier transform to accurately represent the actual A-scan of the sample to be probed, it is important that a sampling rate of the spectrum-resolved interference signal is as high as at least a Nyquist rate. That is, a wavenumber interval between sample wavelengths must be less than the reciprocal of twice the depth range over the entire range of sample wavelengths. This is expressed by the following Formula (7).

[Mathematical Formula 7]

$$\Delta k \leq \frac{1}{2z_{max}} \quad (7)$$

Here, $\Delta k$ is a wavenumber interval between adjacent sampled wavelengths (hereinafter, referred to as sample wavelength) and $z_{max}$ is the maximum depth at which the sample light beam is backscattered. In a case where the sampling rate is lower than that required by the Nyquist rate, the extracted A-scan has aliasing noise. The dependence of the depth range of the A-scan on the wavenumber interval means that the wavelength of the light source should ideally be changed linearly with respect to the wavenumber in time in order to obtain a low-noise A-scan over a long distance.

The majority of SS-OCT systems utilize the swept-source laser as the light source. The wavelength of the swept-source laser is ideal for the SS-OCT because the sweep can be performed continuously over a certain wavelength range. However, the swept-source laser generally relies on a semiconductor laser with tunable external optical components, such as a micro electro mechanical systems (MEMS) reflector or an external optical cavity, to form a laser cavity with a variable size. Such a laser is bulky and expensive to manufacture. In addition, since a complicated manufacturing procedure is required, the cost of the swept-source laser increases. As a result, the SS-OCT system becomes expensive and the potential applications of the SS-OCT are limited.

Furthermore, since the swept-source laser sweeps over an available wavelength range thereof, the wavenumber of the laser generally does not change completely linearly with respect to time. As a result, it is necessary to perform either processing of preparing a non-uniform frequency k-clock signal that notifies a user when to sample the interference signal in order to obtain a uniform wavenumber interval or processing of interpolating the interference signal at a uniform wavenumber interval after collecting the interference signal.

The semiconductor wavelength-tunable laser has been used as an alternative to the swept-source laser to reduce the cost of the SS-OCT and eliminate the need for the k-clock signal and linear interpolation. Examples of the semiconductor wavelength-tunable laser include, but are not limited to, a sampled-grating distributed Bragg reflector (SGDBR) laser and a distributed-feedback (DFB) laser. The wavelength of the semiconductor wavelength-tunable laser can be tuned to a wide range of discrete wavelengths. The semiconductor wavelength-tunable laser is widely applied in telecommunication, such as wavelength division multiplexing. The ability to discretely tune the wavelengths means that the wavelength of the interference spectrum with a constant wavenumber interval can potentially be selected. In addition, some forms of semiconductor wavelength-tunable lasers such as the SGDBR laser exist in all semiconductor architectures, which allows extremely low potential manufacturing costs. The semiconductor wavelength-tunable laser has a longer coherence length than the swept-source laser, and emits output light in a narrow band.

However, the semiconductor wavelength-tunable laser has some limitations in terms of application to the SS-OCT. First, in order to obtain a constant wavenumber interval at the time of wavelength change of the semiconductor wavelength-tunable laser, a complicated control mechanism for precisely controlling input of the semiconductor wavelength-tunable laser on a multivariate space is required. Second, the semiconductor wavelength-tunable laser is generally not stable over the entire variable range thereof, and there is a region where the laser wavelength or power is unstable. The unstable region has to be removed in a post-processing step after the acquisition of the interference signal. The removal of the unstable region also results in aliasing noise and reduces the depth range of the extracted A-scans.

There is still a need for an SS-OCT device that can use the low-cost semiconductor wavelength-tunable laser while avoiding the above problems.

(Principle of Technology of Disclosure)

Next, the principle of the technology of the disclosure will be described. The technology of the disclosure makes it possible to provide an SS-OCT device that enables acquisition of tomographic data with high resolution and a large depth range. The device uses a combination of the semiconductor wavelength-tunable laser as the light source and compressed sensing to obtain the OCT A-scan with high resolution and a large depth range.

The compressed sensing is a technology that enables accurate extraction of a sparse signal in a basis from a limited number of measured values of a non-sparse signal in another basis. A signal represented by a measurement vector y whose value is measured in a measurement basis, a sparse representation of a signal in a sparse basis represented by a vector x (solution vector), and a linear operator (matrix) A that converts the vector x in the sparse basis into the measurement vector y in the measurement basis are represented as in Formula (8).

[Mathematical Formula 8]

$$y = Ax \quad (8)$$

Here, a row of the non-uniform discrete Fourier transform matrix A (hereinafter, simply referred to as transform matrix) corresponds to each sample wavelength, and a column of the transform matrix A corresponds to a position in the propagation direction of the sample light beam. The vector x is a vector of a scattering intensity in the depth range, and the OCT A-scan can be obtained by obtaining the vector x.

Obtaining the sparse representation of the vector x is usually not possible unless there are at least as many measured values as there are elements in x. The compressed sensing allows extraction of the sparse representation x even with a much smaller number of measured values than the number of elements in the vector x, provided that the vector x is sparse, in other words, there are few non-zero elements in the vector x, and the transform matrix A has a low mutual coherence M. The mutual coherence M is given by Formula (9).

[Mathematical Formula 9]

$$M = \sup_{1 \leq i \neq j \leq n} \frac{|a_i^H a_j|}{|a_i||a_j|} \quad (9)$$

Here, $a_i$ represents the column of the transform matrix A, and n represents the number of elements in x. The sparse representation x is extracted by minimizing the number of non-zero elements in x (when using the L0 norm), as described by Formula (10).

[Mathematical Formula 10]

$$\min\|x\|_0 \quad (10)$$

Note that Formula (8) is satisfied here.

In an actual implementation of the compressed sensing, the L1 norm is often minimized instead of the L0 norm. The norm is not limited to the L0 norm and the L1 norm, and a generalized Lp norm (p is 0 or more and 1 or less) can be used.

In a case where the signal in the measurement basis has noise, some implementations of the compressed sensing minimize the least absolute shrinkage and selection operator (LASSO) given by Formula (11).

[Mathematical Formula 11]

$$\min \frac{1}{2}\|Ax - y\|_2^2 + \lambda\|x\|_1 \quad (11)$$

Here, $\lambda$ is a parameter known as a Lagrange multiplier that changes according to the magnitude of noise in the signal. By specifying the vector x that minimizes the LASSO, the OCT A-scan can be obtained. There are various possible implementations of the compressed sensing, and those skilled in the art will appreciate that any of such implementations can be used.

In the SS-OCT, the sample to be probed generally has a limited number of scattering features, and the A-scan can be considered as a sparse signal with very few non-zero elements in a depth basis. On the other hand, the interference signal is not a sparse signal and is generally non-zero for all sampled wavelengths. The Fourier transform, more specifically, the discrete Fourier transform, represents a linear transform in which the A-scan signal is transformed from a sparse depth basis to a non-sparse wavenumber basis. In a case where a plurality of wavelengths at which the interference signal is sampled does not have a constant wavenumber interval between these wavelengths, the non-uniform discrete Fourier transform is a linear operator that transforms the signal from the depth basis to the wavenumber basis. Thus, it is possible to extract the OCT A-scan of a sample with a sparse scattering profile from a limited number of samples of the interference signal using the compressed sensing under the condition that the mutual coherence of the transform matrix is low. Since an exact value of the element in the non-uniform discrete Fourier transform depends on the wavelength at which the interference signal is sampled, the mutual coherence of the non-uniform discrete Fourier transform may be minimized by optimizing selection of the wavelength at which the interference signal is sampled.

The disclosure discloses a combination of the use of the semiconductor wavelength-tunable laser as the laser source and the compressed sensing as means for extracting the OCT A-scan from the interference signal in a standard SS-OCT device to implement a high-resolution and large-depth-range OCT A-scan with a low-cost light source. The use of the semiconductor wavelength-tunable laser makes it possible to precisely control the laser wavelength in time and to use a set of sample wavelengths that results in a transform matrix with the minimal mutual coherence. The application of the compressed sensing enables extraction of the OCT A-scan of the sample with a sparse scattering profile from the interference signal of the sample sampled at wavelengths with a non-uniform wavenumber interval.

The disclosure allows overcoming obstacles to implement a high-quality OCT A-scan in a case of using the semiconductor wavelength-tunable laser as the laser source, that is, the difficulty of achieving a uniform wavenumber interval between wavelengths sampled over the entire wavelength range of the laser, and the instability of the semiconductor wavelength-tunable laser at a specific wavelength within a tunable wavelength range of the semiconductor wavelength-tunable laser. Further, using compressed sensing eliminates the need for the typical k-clocks or interpolation of interference signals in a standard SS-OCT system. The disclosed ability to freely tune the wavelength of the laser source allows the non-uniform discrete Fourier transform with the minimal mutual coherence, thereby further improving the SS-OCT device using the swept-source laser and the compressed sensing and allowing extraction of the OCT A-scan for a sample having a lower sparsity in the scattering profile.

First Example Embodiment

Hereinafter, a first example embodiment will be described with reference to the drawings. The first example embodiment discloses a measurement device according to the technology of the disclosure.

FIG. 1 illustrates an example of the measurement device according to the first example embodiment. A measurement device 10 of FIG. 1 includes at least a semiconductor wavelength-tunable laser 11, an interferometer 12, a photodetector 13, and a control unit 14. Each unit will be described below.

The semiconductor wavelength-tunable laser 11 outputs output light in such a way as to discretely change a wavelength with time.

The interferometer 12 splits the output light output from the semiconductor wavelength-tunable laser 11 into measurement light and reference light and generates interference light by combining and interfering scattered light obtained by irradiating a sample with the measurement light, and the reference light. Specific examples of the interferometer 12 include, but are not limited to, a Michelson interferometer and a Mach-Zehnder interferometer. The photodetector 13 detects the generated interference light and converts the interference light into an electrical signal.

The control unit 14 selects one sample wavelength from a plurality of sample wavelengths as the wavelength of the output light, and sets the selected one sample wavelength in such a way as to sequentially change with time. In this manner, the control unit 14 performs control in such a way that the wavelength of the output light of the semiconductor wavelength-tunable laser 11 discretely changes with time. In addition, the control unit 14 derives a scattering profile of the sample by performing the compressed sensing on the electrical signal obtained for each of the plurality of sample wavelengths. For example, the control unit 14 derives an A-scan (a sparse signal having few non-zero elements) which is the scattering profile by using data of the electrical signal and a transform matrix indicated by each sample wavelength and a position in a propagation direction of a sample light beam. Details thereof are as described above. In addition, the control unit 14 controls the measurement device as a computer to execute each processing.

Figure 2:
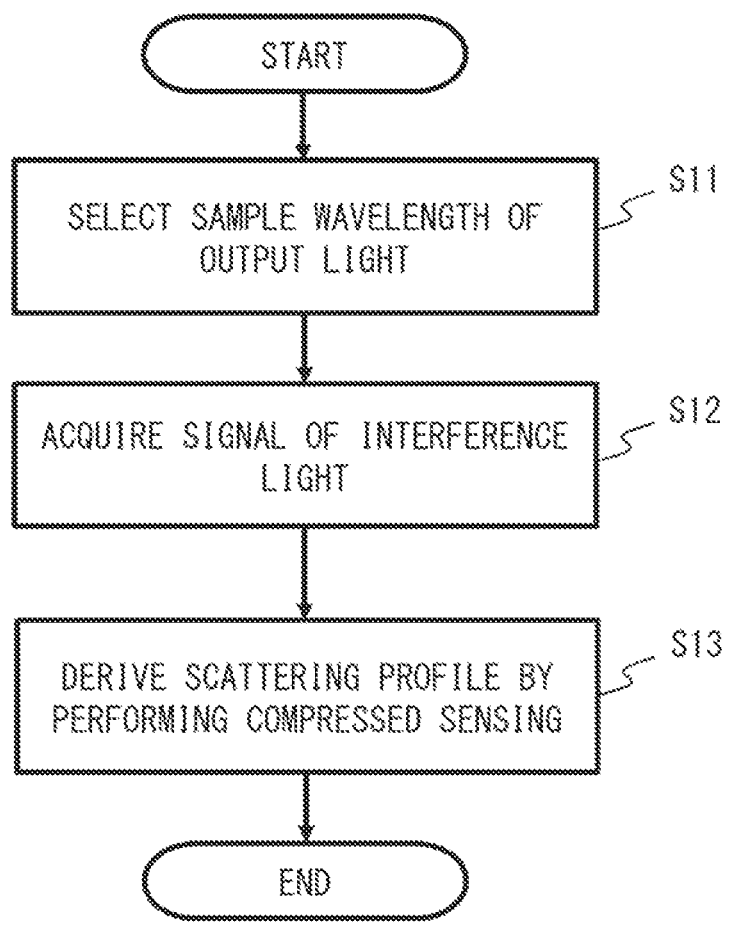
FIG. 2 is a flowchart illustrating a processing example of the measurement device according to the first example embodiment.

FIG. 2 is a flowchart illustrating an example of processing executed by the control unit 14 of the measurement device 10. Each processing will be described below.

First, the control unit 14 selects one sample wavelength from among the plurality of sample wavelengths as the wavelength of the output light, and performs control in such a way that the output light is output in such a way that the selected one sample wavelength discretely and sequentially changes with time (step S11) (control step). The interferometer 12 generates the interference light in which the scattered light obtained by irradiating the sample with the measurement light and the reference light are combined and interfered with each other for the measurement light and the reference light obtained by splitting the output light for each sample wavelength. The interference light is converted into an electrical signal by the photodetector 13.

Next, the control unit 14 acquires the electrical signal obtained by detecting and converting the interference light for each of the plurality of sample wavelengths (step S12) (acquisition step). Then, the control unit 14 derives the scattering profile of the sample by performing the compressed sensing on the electrical signal obtained for each of the plurality of sample wavelengths (step S13) (deriving step).

Here, in step S11, the control unit 14 controls the semiconductor wavelength-tunable laser to output the output light in such a way that parameters related to the plurality of sample wavelengths satisfy the following Formula (12).

[Mathematical Formula 12]

$$\max_{z=z_0, z_1, \ldots z_n} \hat{f}_{samp}(z) \leq \frac{m}{2h-1} \quad (12)$$

However, in Formula (12),

[Mathematical Formula 13]

$$\hat{f}_{samp}(z) \quad (13)$$

is the Fourier transform of a sampling mask related to the plurality of sample wavelengths, z is a specific depth at which a depth profile is extracted, m is the number of the plurality of sample wavelengths, and h is the number of non-zero elements in the vector x of a scattering intensity in a depth range for the scattering profile.

As described above, the measurement device 10 can suppress a decrease in depth range by using the compressed sensing. Details thereof are as described above. Further, a light source in which a sample wavelength of output light discretely and sequentially changes with time can be used as the semiconductor wavelength-tunable laser 11, so that the cost of the light source can be reduced. Further, as shown in Formula (12), since the periodicity of a set of the plurality of sample wavelengths in the wavenumber domain is low, the measurement device 10 can extract the OCT A-scan with high accuracy.

Second Example Embodiment

In the first example embodiment, parameters related to a plurality of sample wavelengths in a wavenumber space may satisfy the following Formula (14).

[Mathematical Formula 14]

$$\max_{z=z_0, z_1, \ldots z_n} \hat{f}_{samp}(z) \leq \frac{m}{2h-1}, \quad (14)$$

for $$\Delta z < z < z_{max}$$

However, in Formula (14), $z_{max}$ is the maximum depth of scattered light, and $\Delta z$ is the solution of a depth profile. Formula (14) is clearly different from Formula (7) described in the related art. According to Formula (14), it is possible to more reliably lower the periodicity of a set of the plurality of sample wavelengths in the wavenumber domain. Therefore, the measurement device 10 can reliably extract the OCT A-scan with high accuracy.

Third Example Embodiment

In the first or second example embodiment, the control unit 14 may execute the following processing in step S13

(deriving step). The control unit 14 defines a measurement vector having a measured value of an electrical signal obtained for each of a plurality of sample wavelengths as a constituent element, a solution vector indicating a scattering profile in a propagation direction of measurement light to a sample, and a non-uniform discrete Fourier transform matrix having a row corresponding to each of the plurality of sample wavelengths and a column corresponding to a position in the propagation direction (definition step). Then, the control unit 14 specifies a sparse representation of the solution vector by using the defined measurement vector and non-uniform discrete Fourier transform matrix (specifying step). As a result, the measurement device 10 can calculate the solution vector without difficulty.

Fourth Example Embodiment

In the third example embodiment, the specifying step may be a step of specifying the sparse representation of the solution vector in which the value of the solution vector minimizes the Lp norm (p is 0 or more and 1 or less) of the solution vector while satisfying a condition that the matrix product of the non-uniform discrete Fourier transform matrix and the solution vector is equal to the measurement vector. As a result, the compressed sensing technology can be easily applied in calculation processing.

Fifth Example Embodiment

In the fourth example embodiment, the Lp norm of the solution vector may be the L1 norm. As a result, it is possible to facilitate calculation in the control unit 14.

Sixth Example Embodiment

In the third example embodiment, the specifying step may be a step of specifying the sparse representation of the solution vector by finding the value of the solution vector that minimizes the LASSO. As a result, the compressed sensing technology can be easily applied in calculation processing.

Seventh Example Embodiment

Hereinafter, a seventh example embodiment will be described with reference to the drawings. In the seventh example embodiment, a more specific application example of the measurement device according to each example embodiment will be described.

Figure 3:
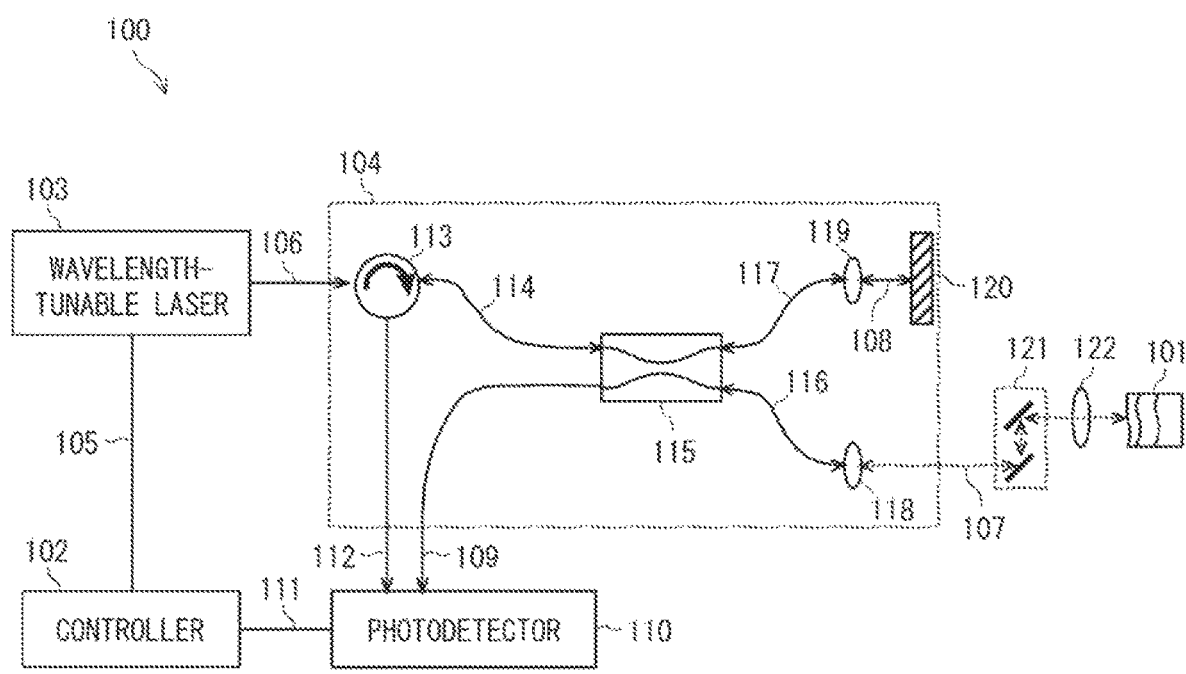
FIG. 3 is a configuration diagram illustrating an example of a SS-OCT device according to a seventh example embodiment.

FIG. 3 illustrates an example of an SS-OCT device according to the seventh example embodiment. An SS-OCT device 100 of FIG. 3 generates 3D tomographic data of an arbitrary sample 101. The SS-OCT device 100 includes at least a controller 102, a semiconductor wavelength-tunable laser 103, an interferometer 104, and a photodetector 110.

The controller 102 corresponds to the control unit 14 of the first example embodiment, and outputs a control signal 105 to the semiconductor wavelength-tunable laser 103 to determine the wavelength and power of laser light 106 emitted from semiconductor wavelength-tunable laser 103. The controller (control unit) 102 outputs the control signal 105 in such a way as to change with time, thereby discretely changing the wavelength of the laser light 106 emitted from the semiconductor wavelength-tunable laser 103 with time.

The semiconductor wavelength-tunable laser 103 corresponds to the semiconductor wavelength-tunable laser 11 of the first example embodiment, and outputs the laser light 106 in such a way that the wavelength changes discretely with time according to the control signal 105. The laser light 106 is incident on the interferometer 104.

The interferometer 104 corresponds to the interferometer 12 of the first example embodiment and generates interference light by using the laser light 106. In detail, the laser light 106 is split into at least two light beams in the interferometer 104. At least one of the split light beams is a sample light beam 107 and at least the other one of the split light beams is a reference light beam 108. The sample 101 is irradiated with the sample light beam 107 and the sample light beam 107 backscattered by the sample 101 is returned to the interferometer 104. The returned sample light beam 107 interferes with the reference light beam 108 to generate at least one optical interference signal 109.

The photodetector 110 corresponds to the photodetector 13 of the first example embodiment, detects the optical interference signal 109 for each sample wavelength, and converts the signal into an electrical interference signal 111. The electrical interference signal 111 is output to the controller 102. The controller 102 applies the compressed sensing to extract an OCT A-scan from the electrical interference signal 111.

As an example, there may be a second optical interference signal 112 separately from the first optical interference signal 109. In this case, the second optical interference signal 112 is complementary to the first optical interference signal 109, and the photodetector 110 is a balanced detector. The first optical interference signal 109 and the second optical interference signal 112 are converted into the electrical interference signal 111 as described above, and the controller 102 extracts the OCT A-scan from the electrical interference signal 111.

Hereinafter, a specific example of the interferometer 104 will be further described. In this example, the interferometer 104 is an optical fiber Michelson interferometer, and the interferometer 104 includes an optical circulator 113, an intermediate fiber 114, a coupler 115, a sample optical fiber 116, a reference optical fiber 117, a sample collimator lens 118, a reference collimator lens 119, and a reference mirror 120.

The laser light 106 passes through an optical fiber cable (that is, the laser light 106 is coupled to the optical fiber cable) and is transmitted to the optical circulator 113. The optical circulator 113 may output the second optical interference signal 112 described above in addition to outputting the passing laser light 106 to the intermediate fiber 114. The laser light 106 reaches the coupler 115 via the intermediate fiber 114. The coupler 115 splits the laser light 106 into the sample light beam 107 coupled to the sample optical fiber 116 and the reference light beam 108 coupled to the reference optical fiber 117.

The sample collimator lens 118 at an end portion of the sample optical fiber 116 on a side opposite to an end portion of the sample optical fiber 116 that is adjacent to the coupler 115 collimates the sample light beam 107 for irradiating the sample 101. The backscattered light from the sample 101 is collected by the sample collimator lens 118, is coupled to the sample optical fiber 116, and returns to the coupler 115.

In one example, the sample light beam 107, which is a beam, first passes through a scanner 121 and an objective lens 122 to irradiate the sample 101. The scanner 121 is used to change an angle at which the sample light beam 107 is incident on the objective lens 122. The objective lens 122 focuses the sample light beam 107 onto the sample 101. Therefore, the scanner 121 changes the angle at which the sample light beam 107 is incident on the objective lens 122, thereby changing a lateral position on the sample 101 to which the sample light beam 107 is focused. A 3D tomographic image of the sample 101 is generated by acquiring the OCT A-scan for each lateral position on the sample 101.

Meanwhile, the reference collimator lens 119 at an end portion on a side opposite to an end portion of the reference optical fiber 117 that is adjacent to the coupler 115 collimates the reference light beam 108 and irradiates the reference mirror 120 with the reference light beam. The reference mirror 120 reflects the reference light beam 108, the reflected light of which is collected by the reference collimator lens 119, is coupled to the reference optical fiber 117, and returns to the coupler 115. The reflected reference light beam 108 and the backscattered light from the sample interfere within the coupler 115 and generate the first optical interference signal 109. The first optical interference signal 109 is input to and detected by the photodetector 110. Meanwhile, the second optical interference signal 112, which is a complementary optical signal, passes through the intermediate fiber 114 and the optical circulator 113 and is input to and detected by the photodetector 110.

In an example, the controller 102 includes a processor, at least one digital-to-analog converter (DAC), and at least one analog-to-digital converter (ADC). The processor transmits a digital signal to the at least one DAC, and the DAC generates the control signal 105 based on the digital signal. The control signal 105 can include a single-channel signal or a multi-channel signal that depends on an architecture of the semiconductor wavelength-tunable laser 103 and means for controlling the wavelength and output power of the laser light 106 emitted by the semiconductor wavelength-tunable laser 103.

The electrical interference signal 111 input to the controller 102 is converted into a digital interference signal by the ADC, and the digital interference signal is output to the processor. The processor then applies the compressed sensing to extract an OCT A-scan from the digital interference signal. The processor may be a field programmable gate array, a computer, a microcontroller, or any other computing device.

Figure 4:
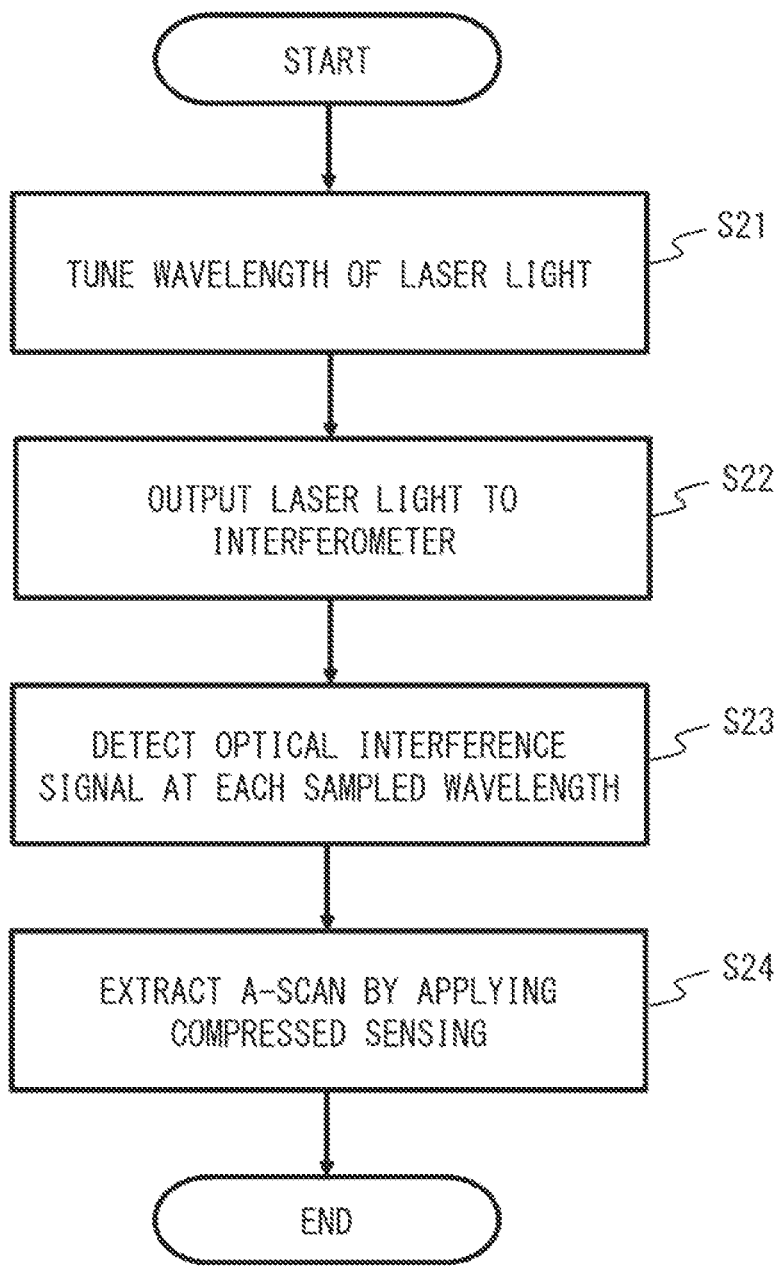
FIG. 4 is a flowchart illustrating an example of a process for acquiring an OCT A-scan according to the seventh example embodiment.

FIG. 4 is a flowchart illustrating an example of processing for the SS-OCT device 100 to acquire the OCT A-scan by using the semiconductor wavelength-tunable laser and the compressed sensing. Hereinafter, each processing of the process will be described with reference to FIG. 4.

First, the controller 102 outputs the control signal 105 to tune the wavelength of laser light emitted by the semiconductor wavelength-tunable laser 103 to a sequence including a plurality of sample wavelengths over a certain period (step S21). Here, each wavelength at which the laser light is tuned is referred to as a sample wavelength. The wavelength of the laser light may be kept constant for a period until the wavelength changes to another sample wavelength. That is, the wavelength of the laser light may change stepwise in time-series data. The period until a certain sample wavelength changes to another sample wavelength may be constant or may change for each sampled wavelength.

The semiconductor wavelength-tunable laser 103 outputs the laser light 106 to the interferometer 104 at the wavelength set in step S201 (step S22). The output laser light passes through the interferometer 104 and moves on one of two optical paths. In one optical path within the interferometer 104, the sample 101 is irradiated with the sample light beam 107 and the backscattered light from the sample returns to the interferometer 104. The other optical path is an optical path through which the reference light beam 108 passes (see FIG. 3).

The photodetector 110 detects (measures), at each sample wavelength, the optical interference signal 109 generated by interference of the reference light beam 108 with the back-scattered light from the sample 101 (step S23). The photodetector 110 converts the optical interference signal 109 into the electrical interference signal 111 for each sample wavelength, and outputs the electrical interference signal 111 to the controller 102.

The controller 102 generates a digital interference signal from the electrical interference signal 111 and extracts the OCT A-scan of the sample from the interference signal measured at each sample wavelength by applying the compressed sensing to the digital interference signal (step S24). A detailed method of the compressed sensing is as described above.

Various possible implementations of the compressed sensing include, but are not limited to, specifying an A-scan with the minimum L0 norm, specifying an A-scan with the minimum L1 norm, specifying an A-scan with the minimum LASSO, and the like, as examples. As described above, the norm is not limited to the L0 norm and the L1 norm, and a generalized Lp norm (p is 0 or more and 1 or less) can be used. The compressed sensing may be performed after measurement of the interference signal. The interference signal may be stored in the controller 102 for later post-processing.

In a case where the lateral position of the sample light beam is scanned using the SS-OCT device to acquire 3D data, the compressed sensing may be performed on the interference signal obtained for one position on the sample before moving the sample light beam to a new position on the sample. Alternatively, the compressed sensing may be performed at any timing after measurement of the interference signal without considering a timing of scanning of the sample light beam.

Figure 5:
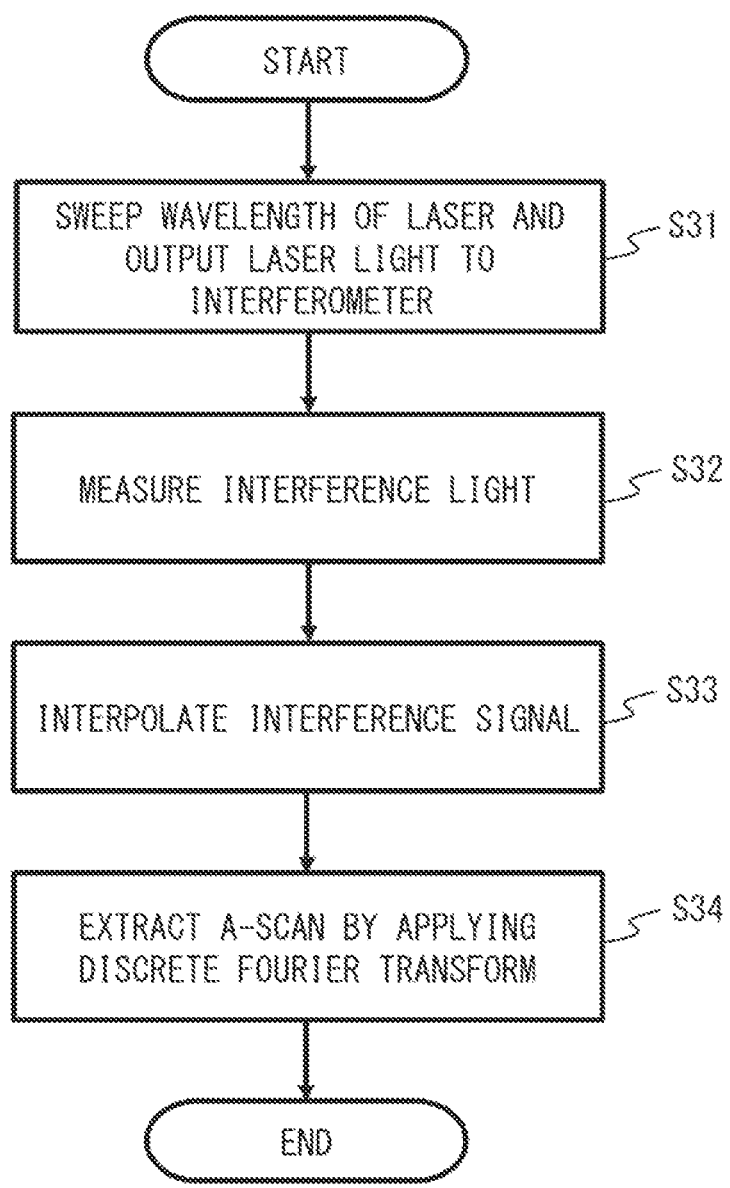
FIG. 5 is a flowchart illustrating an example of a method of extracting an OCT A-scan according to the related art.
Figure 6A:
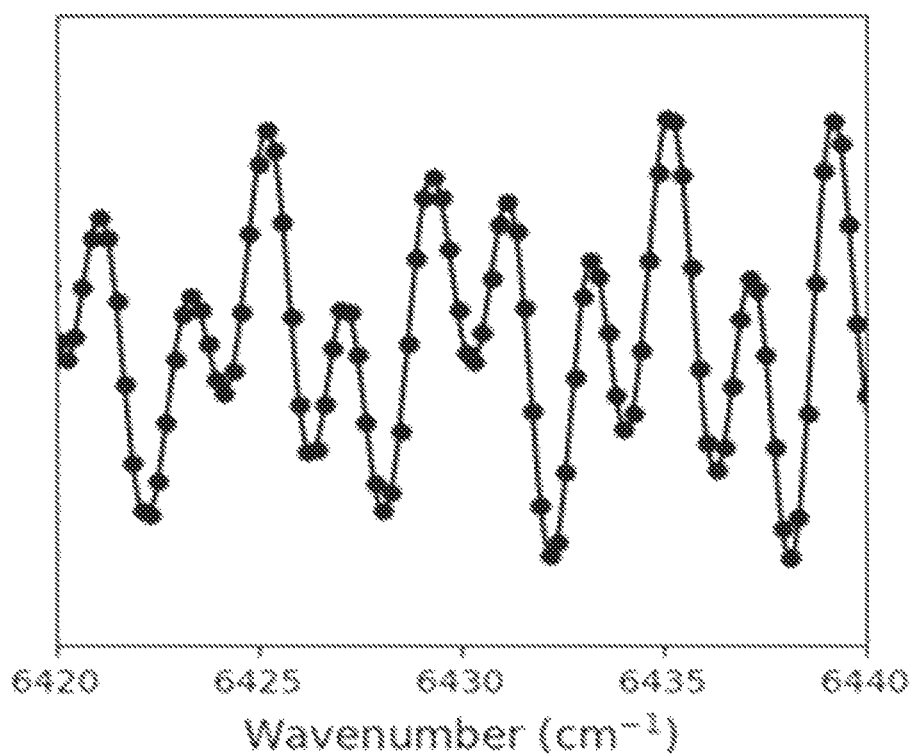
FIG. 6A is a graph illustrating an example of a measured value of an interference signal according to the related art.
Figure 6B:
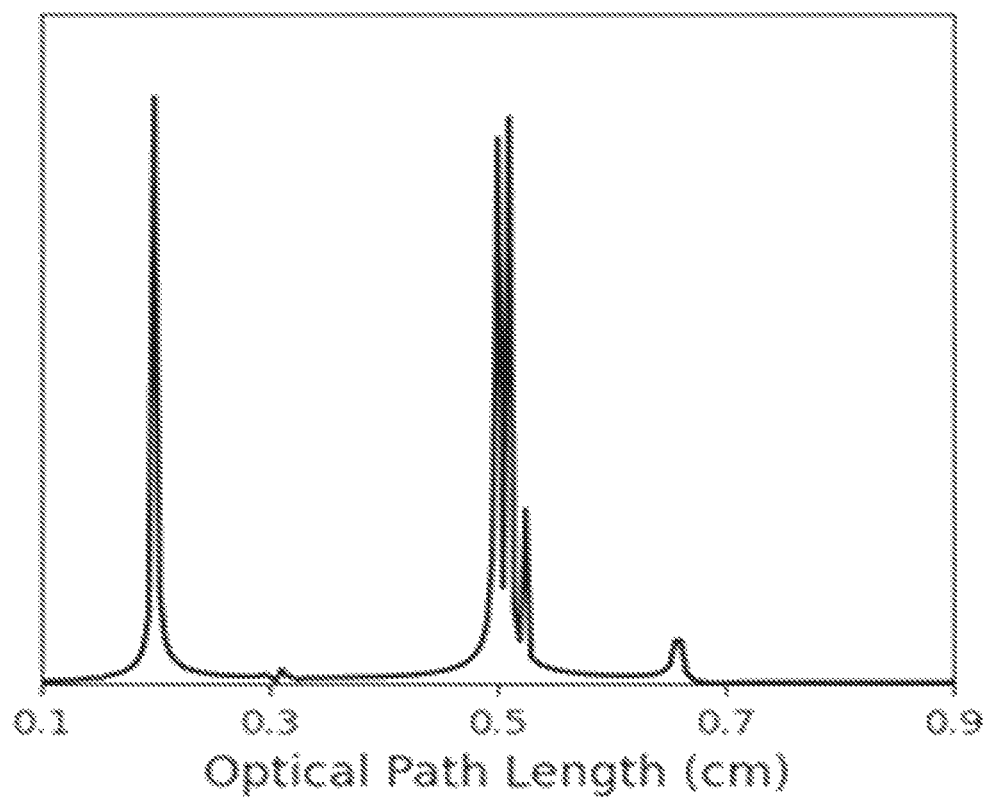
FIG. 6B is a graph illustrating an example of the OCT A-scan according to the related art.
Figure 6C:
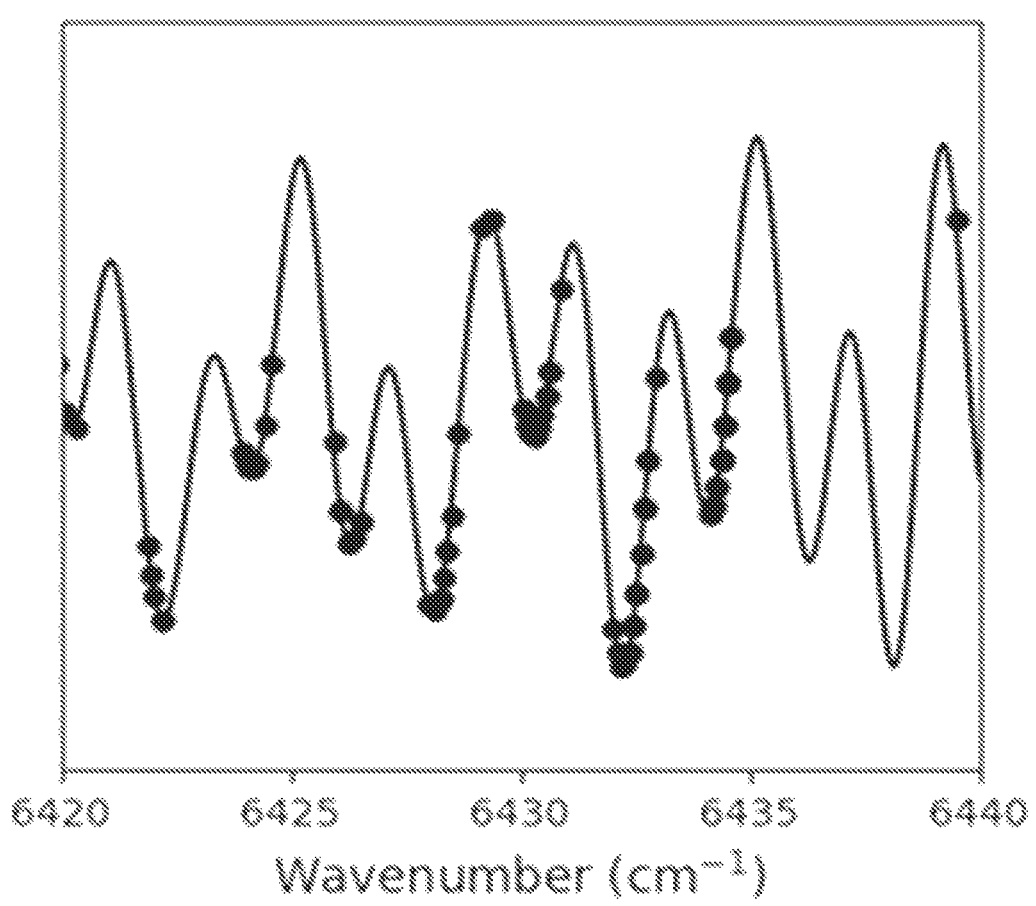
FIG. 6C is a graph illustrating an example of the interference signal in a case where the interference signal is sampled at a non-constant wavenumber interval in the related art.
Figure 6D:
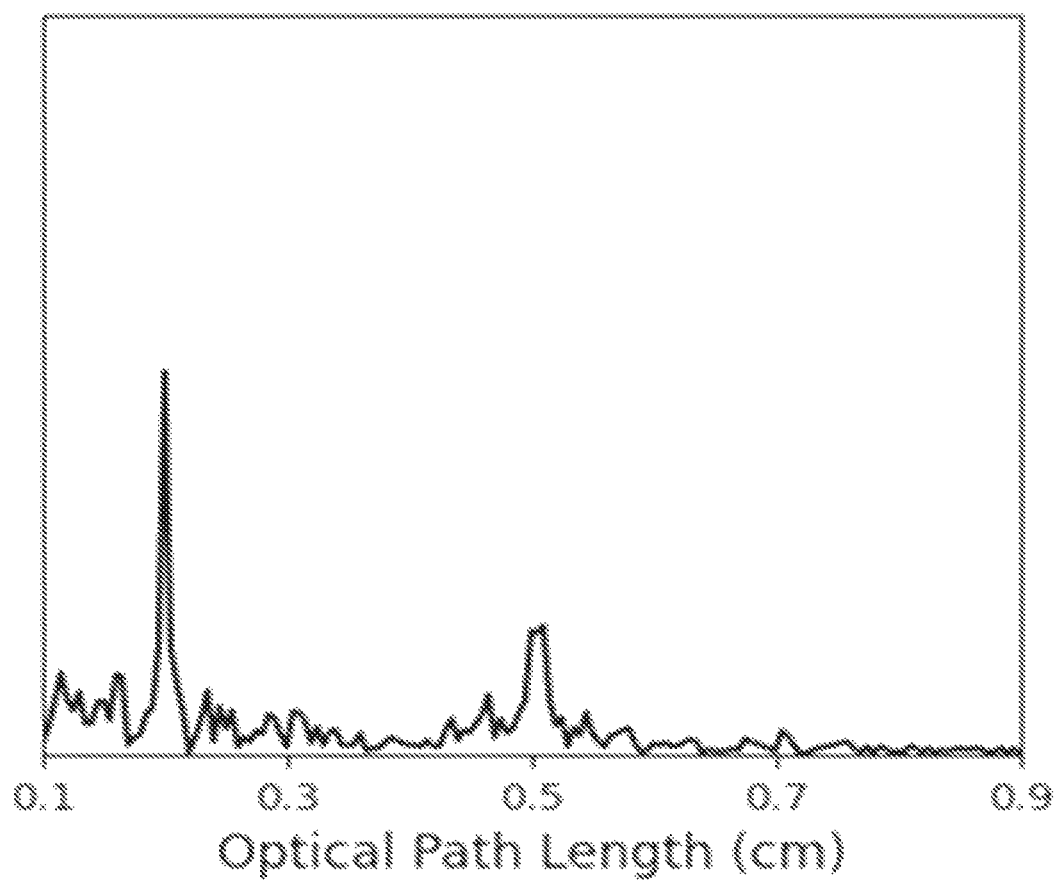
FIG. 6D is a graph illustrating an example of the OCT A-scan in a case where the interference signal is sampled at a non-constant wavenumber interval in the related art.

FIGS. 5 and 6A to 6D illustrate a standard method for obtaining an OCT A-scan in a standard SS-OCT device according to the related art described above. In particular, FIG. 5 is a flowchart for describing an example of the standard method of extracting an OCT A-scan. FIG. 6A is a graph illustrating an example of the measured value of the interference signal in an ideal case where the interference signal is sampled at a constant interval at a rate exceeding the Nyquist rate. FIG. 6B illustrates an example of the OCT A-scan obtained using the standard method in the ideal case. FIG. 6C illustrates an example of a graph of the interference signal in a case where the interference signal is sampled at a non-constant wavenumber interval by using the semiconductor wavelength-tunable laser as a laser source. FIG. 6D illustrates an example of the OCT A-scan obtained using the standard method in a case where the wavenumber interval is not constant, with the semiconductor wavelength-tunable laser as the laser source. Hereinafter, the OCT A-scan obtained by the related art will be described with reference to FIGS. 5 and 6A to 6D for comparison with the SS-OCT device 100 described in the second example embodiment.

Referring to FIG. 5, first, the SS-OCT device sweeps the wavelength of a laser over a predetermined wavelength range and outputs the laser light to an interferometer (step S31). The swept laser light passes through the interferometer. In one optical path within the interferometer, a sample is irradiated with the laser light, and backscattered light from the sample is collected in the optical path. The other optical path within the interferometer is an optical path for a reference light laser. Interference between reference light and the backscattered light from the sample generates interference light.

The SS-OCT device measures the interference light generated by the interferometer (step S32). The SS-OCT device may measure an interference signal at a constant time interval (that is, a constant wavenumber interval), or may trigger measurement by using a k-clock and obtain measured values at a plurality of wavelengths at a constant wavenumber interval.

In a case where the interference signal is measured at a constant time interval, the SS-OCT device interpolates the interference signal at a constant wavelength interval (step S33). In a case where the k clock is used to obtain the constant time interval, step S33 is skipped. The SS-OCT device extracts an A-scan by taking a discrete Fourier transform of the interference signal at a constant wavenumber interval (step S34).

In FIG. 6A, an example of a theoretical interference signal generated by the sample is indicated by a solid line, and a measured value of the theoretical interference signal at a constant wavenumber interval is indicated by a dot. FIG. 6B illustrates an OCT A-scan obtained by performing the discrete Fourier transform on the measured values at the constant wavenumber interval illustrated in FIG. 6A. In FIGS. 6A and 6B, a scattering profile of the sample is accurately reflected in the obtained OCT A-scan.

However, in a case where the wavenumber interval between sample wavelengths is not constant, such as a case using the semiconductor wavelength-tunable laser, the scattering profile of the sample is not accurately reflected in the OCT A-scan in some cases. In FIG. 6C, an example of the theoretical interference signal generated by the sample is indicated by a solid line, and a measured value of the interference signal measured in a case where the wavenumber interval between the sample wavelengths is not constant is indicated by a dot. The solid line graph in FIG. 6C is the same as the solid line graph in FIG. 6A. As compared with FIG. 6A, in FIG. 6C, it can be seen that the measured values of the interference signal are detected in a biased way.

FIG. 6D illustrates an OCT A-scan obtained by interpolating the measured values illustrated in FIG. 6C at a constant wavenumber interval and then performing the discrete Fourier transform. As can be seen by comparing FIGS. 6B and 6D, in FIG. 6D, the fine structural details of the scattering profile of the sample are lost and aliasing noise occurs in the OCT A-scan.

However, this problem can be solved by using the compressed sensing. The ability of the compressed sensing to extract an OCT A-scan from an interference signal sampled at a non-uniform wavenumber interval will be described with reference to FIGS. 7A and 7B.

Figure 7A:
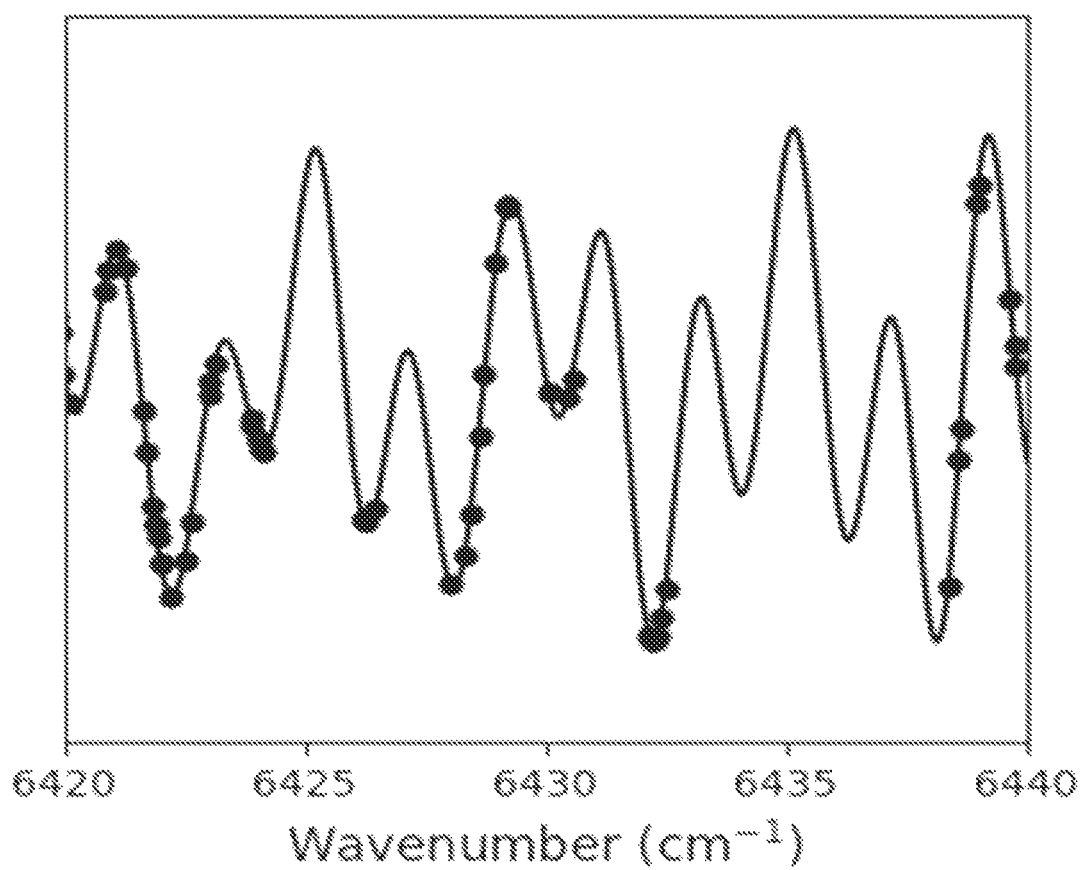
FIG. 7A is a graph illustrating an example of the measured values of the interference signals sampled at one set of randomly distributed wavelengths.

In FIG. 7A, an example of the theoretical interference signal generated by the sample is indicated by a solid line, and a measured value of the interference signal sampled at a set of wavelengths randomly distributed over the entire variable wavelength range of the semiconductor wavelength-tunable laser is indicated by a dot. The solid line graph in FIG. 7A is the same as the solid line graph in FIGS. 6A and 6C.

Figure 7B:
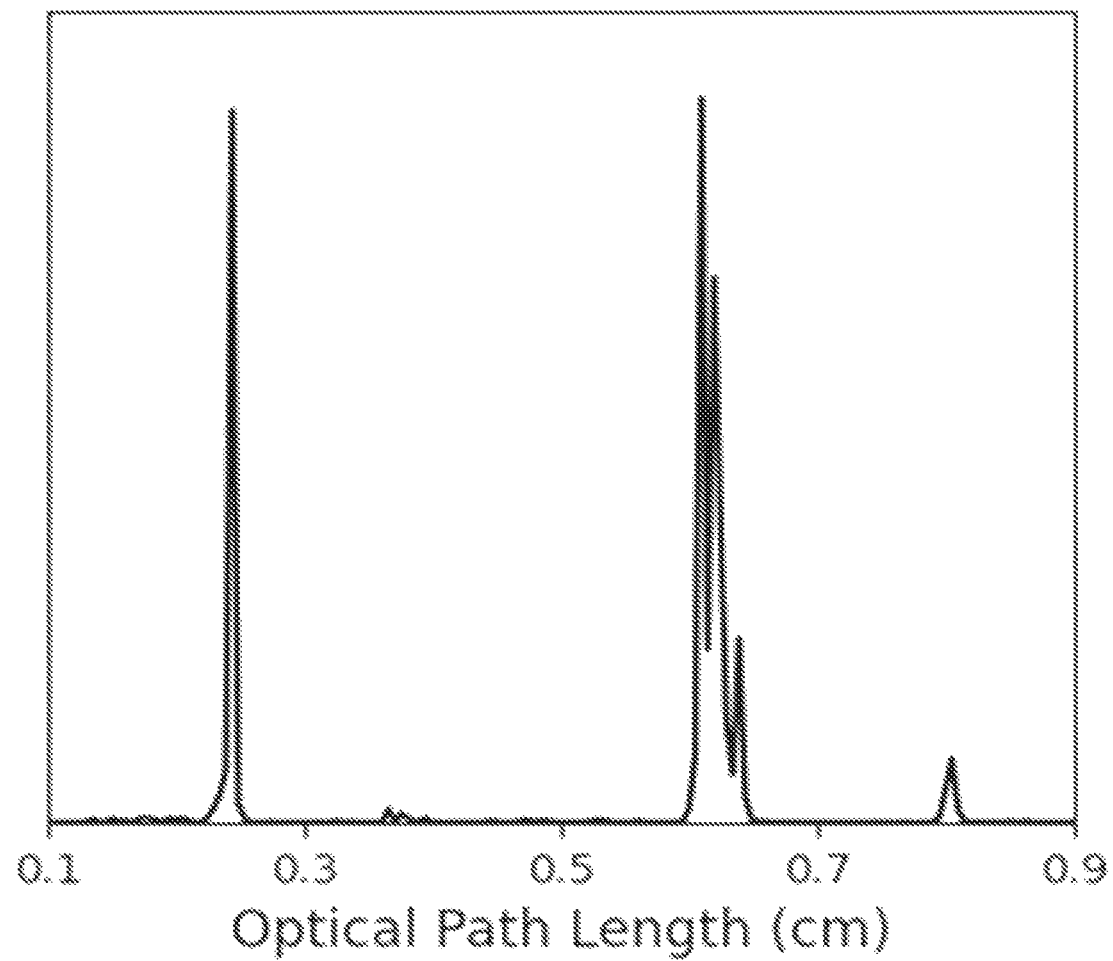
FIG. 7B is a graph illustrating an example of the OCT A-scan obtained by applying compressed sensing to the measured value.

FIG. 7B illustrates an OCT A-scan obtained by applying the compressed sensing to the measured values illustrated in FIG. 7A. As can be seen by comparing FIG. 7B with FIGS. 6B and 6D, the fine structural details of the scattering profile of the sample are accurately reproduced, and aliasing noise is suppressed by applying the compressed sensing.

One important criterion for the accuracy of the OCT A-scan extracted using the compressed sensing is a low mutual coherence of transform matrices. Specifically, in a case where the mutual coherence M of the transform matrices is as in the following Formula (15), when applying the compressed sensing, an OCT A-scan having h non-zero elements or less can be extracted.

[Mathematical Formula 15]

$$M \le 1/h \tag{15}$$

In a case where the L1 norm or LASSO is used, instead of Formula (15), the following Formula (16) is a condition related to the mutual coherence M.

[Mathematical Formula 16]

$$M \le \frac{1}{2h-1} \tag{16}$$

In practice, the OCT A-scan can be extracted with high accuracy even in a case where the mutual coherence is higher than that required by Formula (15) (or Formula (16)). However, it remains the fact that as the mutual coherence decreases, it is possible to extract an A-scan with more non-zero elements.

For the non-uniform discrete Fourier transform, selection of the sample wavelength dominates the mutual coherence of the matrices. In a case where a set of sample wavelengths has periodicity in its value in the wavenumber domain, the transform matrices have a high mutual coherence. On the other hand, in a case where a set of sample wavelengths has no periodicity in its value in the wavenumber domain, the mutual coherence is low. The values of the sample wavelengths randomly distributed over a certain range are an example of a set of sample wavelength values that have very low periodicity and result in transform matrices having a low mutual coherence.

The periodicity of the values of the set of sample wavelengths in the wavenumber domain can be quantified as follows. First, the sampling mask of the sample wavelength is defined as follows. The value of the sampling mask is 1 at a wavenumber at which the corresponding sample wavelength exists, and is 0 at a wavenumber at which the corresponding sample wavelength does not exist. A wavenumber corresponding to a certain wavelength is simply the reciprocal of the wavelength. The Fourier transform of the sampling mask is expressed by the following Formula (17):

[Mathematical Formula 17]

$$\hat{f}_{samp}(z) = F\{f_{samp}(k)\}. \tag{17}$$

[Mathematical Formula 18]

$$\hat{f}_{samp}(z), \tag{18}$$

which is the left-hand side of Formula (17), is the Fourier transform of the sampling mask, $f_{samp}(k)$ on the right-hand side is the sampling mask, and F indicates an operation of the Fourier transform. The set of the sample wavelength values is sufficiently aperiodic in a case where the Fourier transform of the sampling mask is as in the following Formula (19).

[Mathematical Formula 19]

$$\max_{z=z_0, z_1, \ldots z_n} \hat{f}_{samp}(z) \le \frac{m}{2h-1} \quad (19)$$

Here, z ($z_0$, $z_1$, ..., and $z_n$) is the specific depth from which the depth profile is extracted, m is the number of sample wavelength values, and h is as described above. Just like the mutual coherence, in practice, the OCT A-scan can be extracted with high accuracy even in a case where the periodicity is higher than that required by Formula (19) in some cases. However, in a case where the periodicity satisfies the condition of Formula (19), the OCT A-scan can be reliably extracted with high accuracy.

In addition, the parameters related to the plurality of sample wavelengths in the wavenumber space preferably satisfy the following Formula (20).

[Mathematical Formula 20]

$$\max_{z=z_0, z_1, \ldots z_n} \hat{f}_{samp}(z) \le \frac{m}{2h-1}, \quad (20)$$

for $$\Delta z < z < z_{max}$$

Here, $z_{max}$ is the maximum depth at which the sample light beam is backscattered, as described above, and $\Delta z$ is the solution of the depth profile. The wavenumber interval is larger than that in Formula (7) described for the related art. Therefore, in Formula (20), the sample wavelengths exist more discretely in the wavenumber space as compared with Formula (7). Therefore, the periodicity of a set of sample wavelengths in the wavenumber domain can be more reliably lowered.

In the following, for illustration purposes, FIGS. 8A to 8E are used to illustrate the effect of the periodicity of a set of the sample wavelengths on the accuracy of the OCT A-scan obtained using the compressed sensing.

Figure 8A:
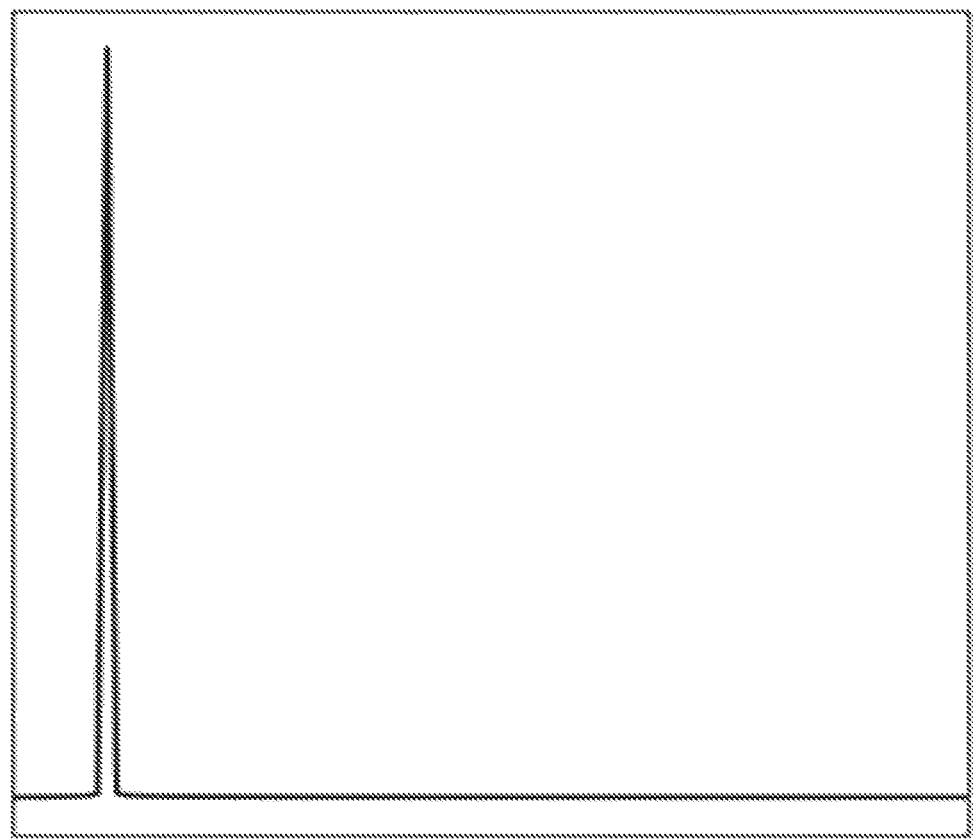
FIG. 8A is a graph illustrating an example of the OCT A-scan of an ideal sample.

FIG. 8A illustrates an example of an OCT A-scan of an ideal sample with a single scattering point. It can be said that the closer the result obtained as the OCT A-scan is to this graph, the higher the accuracy of the method is.

Figure 8B:
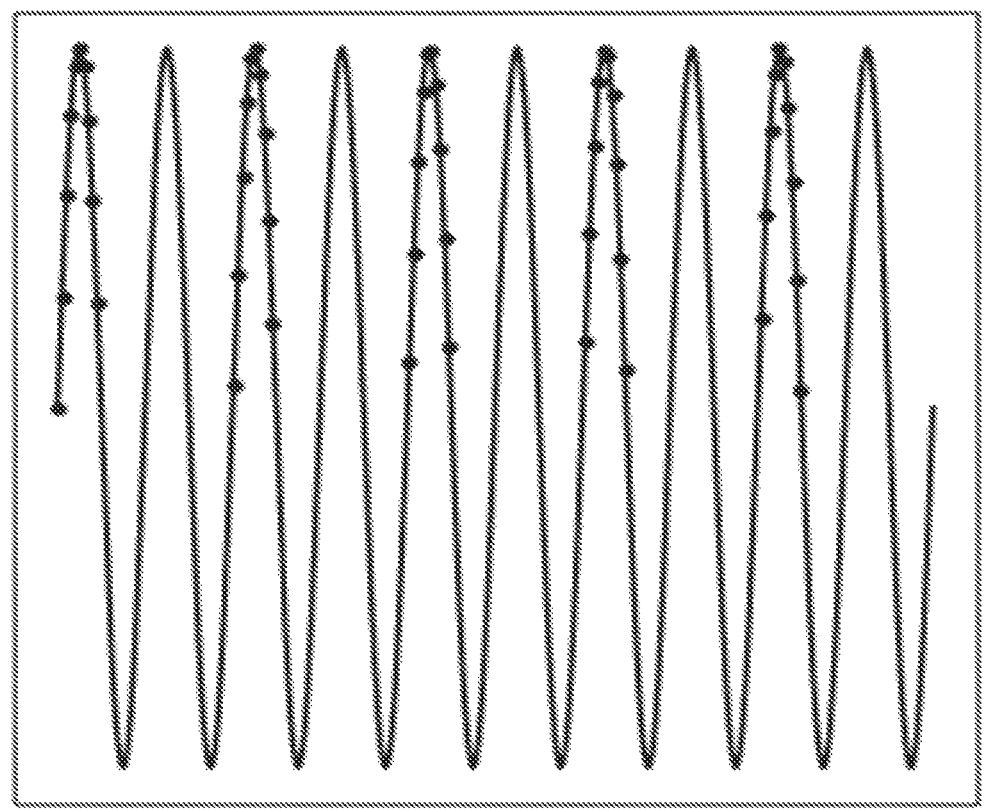
FIG. 8B is a graph illustrating an example of the measured value of the interference signal in a case where there is a periodic gap in a sample wavelength.

FIG. 8B illustrates an example of a measured value of the interference signal in a case where the interference signal is sampled at the Nyquist rate (that is, at a high resolution) but there is a periodic gap in the sample wavelength. In FIG. 8B, an example of the interference signal is indicated by a solid line, and the measured value of the sampled interference signal is indicated by a dot.

Figure 8C:
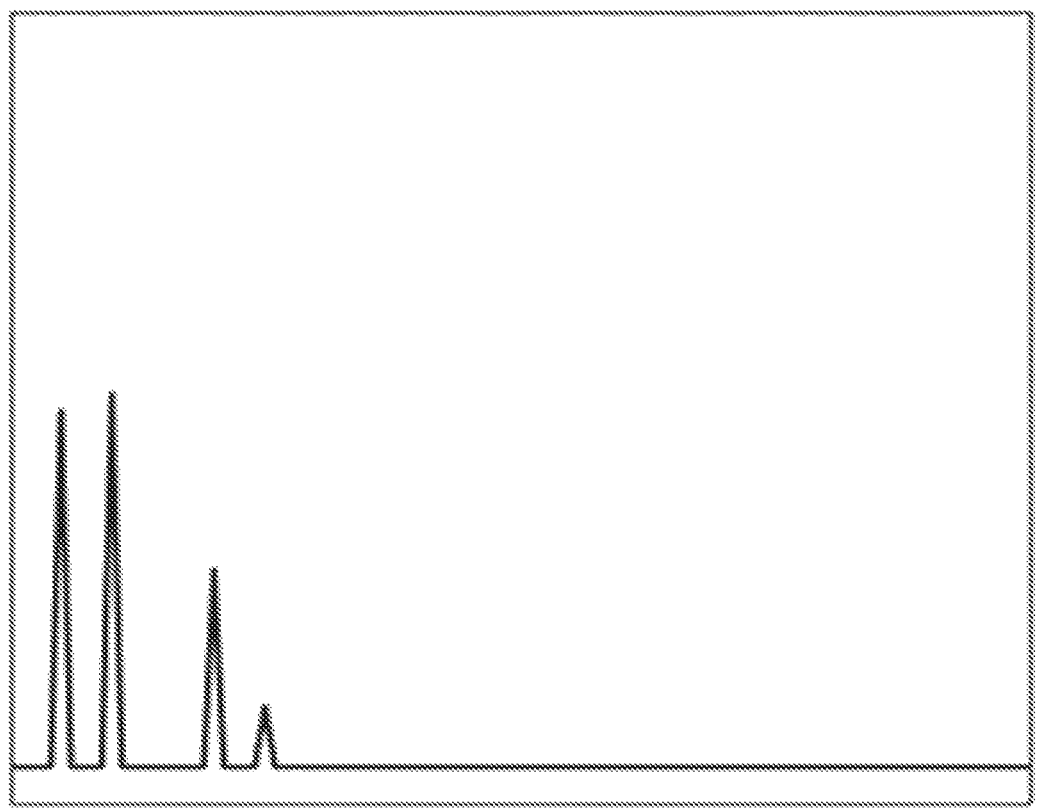
FIG. 8C is a graph illustrating an example of the OCT A-scan extracted from a set of sample wavelengths illustrated in FIG. 8B by using the compressed sensing.

FIG. 8C illustrates an example of an OCT A-scan extracted from a set of the sample wavelengths illustrated in FIG. 8B by using the compressed sensing. It can be clearly seen from FIG. 8C that there are three spurious peaks in the OCT A-scan result.

Figure 8D:
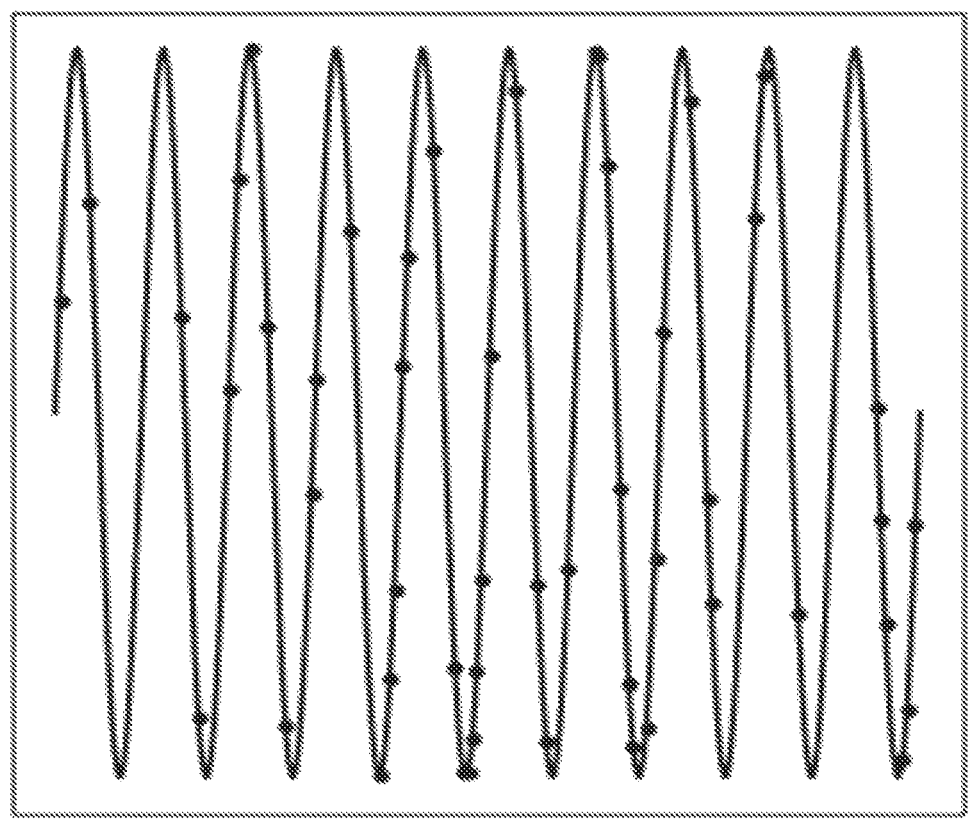
FIG. 8D is a graph illustrating an example of the measured value of the interference signal in a case where the interference signal is sampled at randomly distributed sample wavelengths.

FIG. 8D illustrates an example of the measured value of the interference signal in a case where the interference signal is sampled at randomly distributed sample wavelengths (that is, in a state where the periodicity of the values of the sample wavelengths is low). In FIG. 8D, an example of the interference signal is indicated by a solid line, and the measured value of the sampled interference signal is indicated by a dot. The solid line graph in FIG. 8D is the same as the solid line graph in FIG. 8B.

Figure 8E:
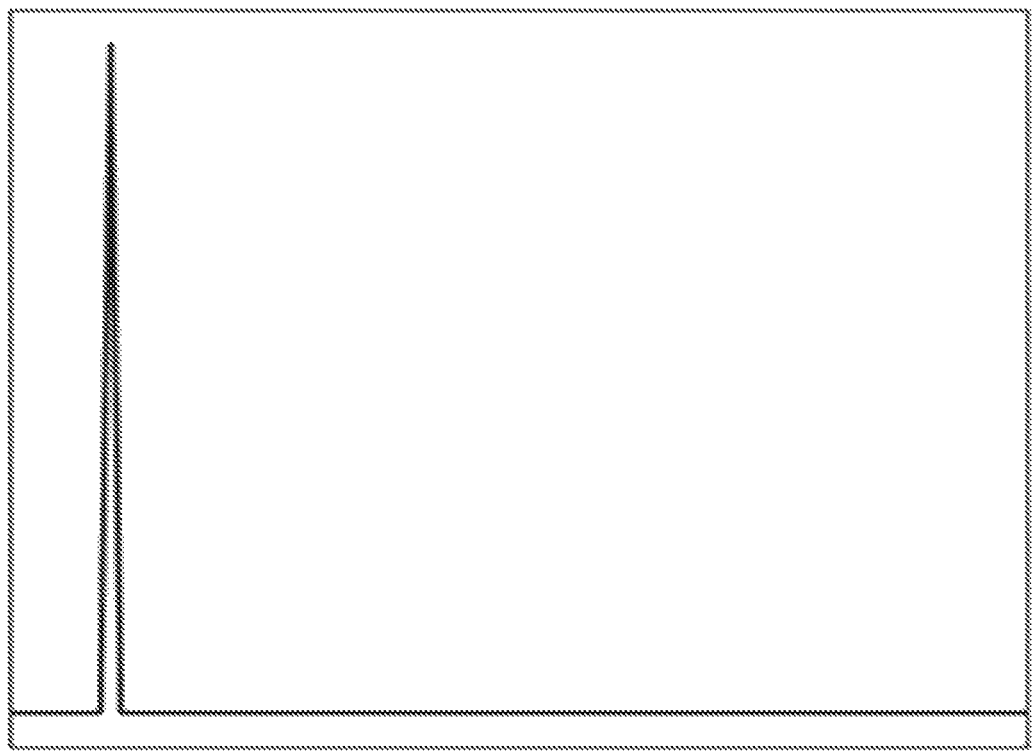
FIG. 8E is a graph illustrating an example of the OCT A-scan extracted from a set of sample wavelengths illustrated in FIG. 8D by using the compressed sensing.

FIG. 8E illustrates an example of an OCT A-scan extracted from a set of the sample wavelengths illustrated in FIG. 8D by using the compressed sensing. FIG. 8E illustrates that no spurious peak as in FIG. 8C exist in the OCT A-scan result and there is a single scattering point at the same place as in FIG. 8A. As described above, it has been described that the sample wavelengths with low periodicity is important to obtain an accurate OCT A-scan.

An example of a method for obtaining a set of the sample wavelengths with low periodicity by using the semiconductor wavelength-tunable laser will be described below with reference to FIGS. 9 and 10A to 10E.

Figure 9:
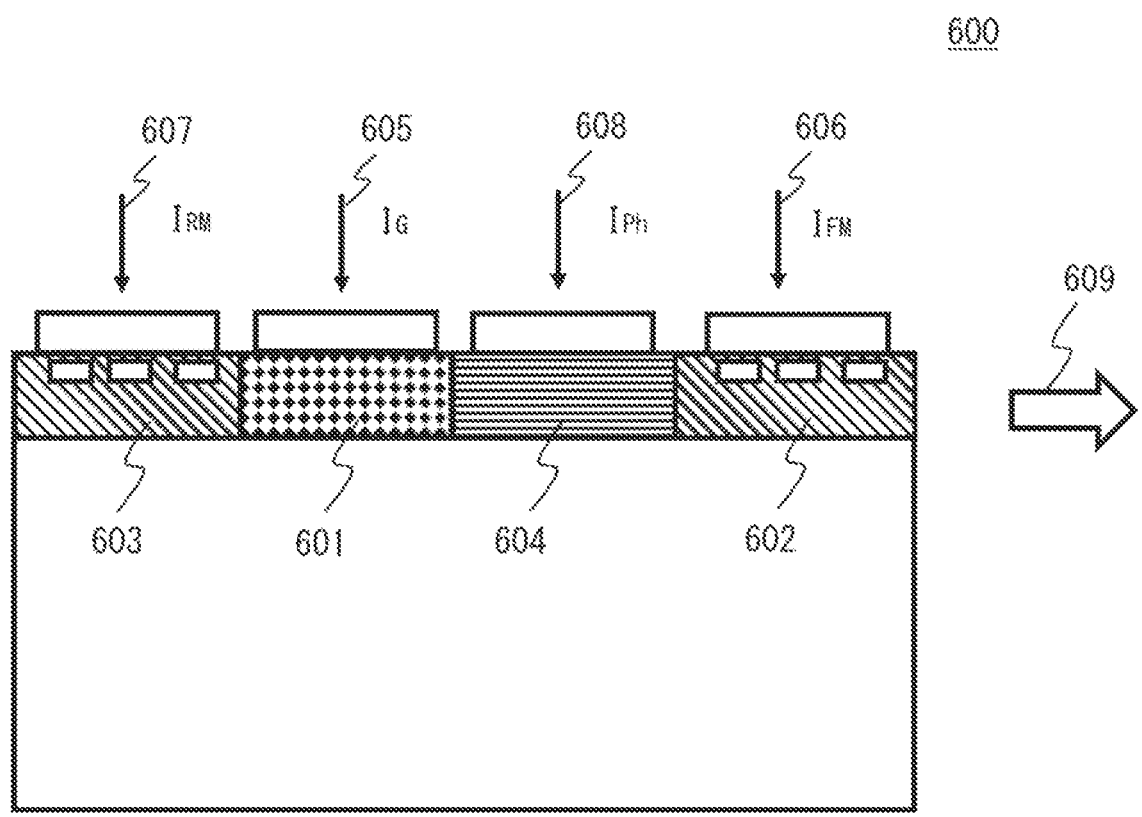
FIG. 9 is a schematic diagram of a SGDBR laser according to the seventh example embodiment.

FIG. 9 is a schematic diagram of a sampled-grating distributed Bragg reflector (SGDBR) laser which is a type of semiconductor wavelength-tunable laser. An SGDBR laser 600 includes a laser gain medium 601, a so-called front mirror 602 that is a first SGDBR, a so-called rear mirror 603 that is a second SGDBR, and a phase shifter device 604. The power and wavelength of laser light 609 emitted from the SGDBR laser 600 are determined by a current $I_G$ 605, a current $I_{FM}$ 606, a current $I_{RM}$ 607, and a current $I_{Ph}$ 608 input to the laser gain medium 601, the front mirror 602, the rear mirror 603, and the phase shifter device 604, respectively.

In the SS-OCT device 100 of FIG. 3, the SGDBR laser 600 can be applied to the semiconductor wavelength-tunable laser 103. Here, the laser light 609 corresponds to the laser light 106. In addition, each of the current $I_G$ 605 to the current $I_{Ph}$ 608 has a value corresponding to the wavelength and power of the output light that changes with time, which is determined by the controller 102.

Figure 10A:
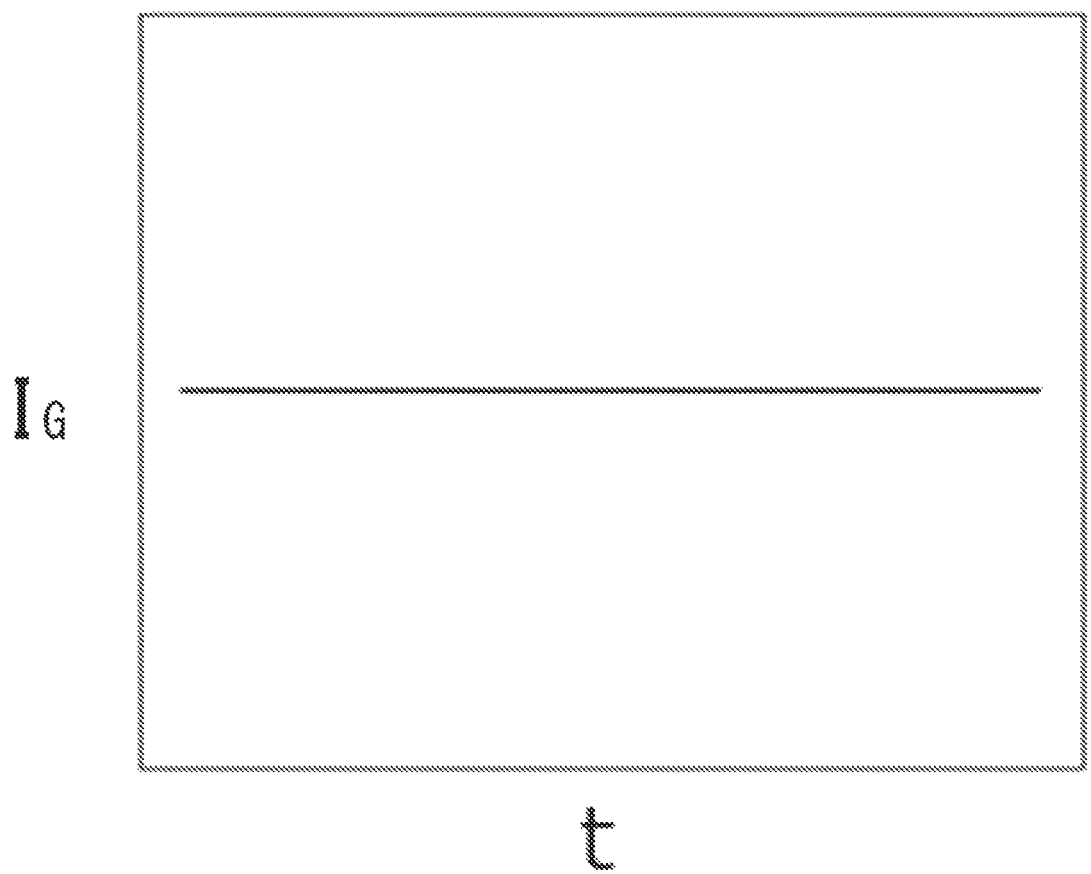
FIG. 10A is a graph illustrating an example in which a current $I_G$ changes with time according to the seventh example embodiment.
Figure 10B:
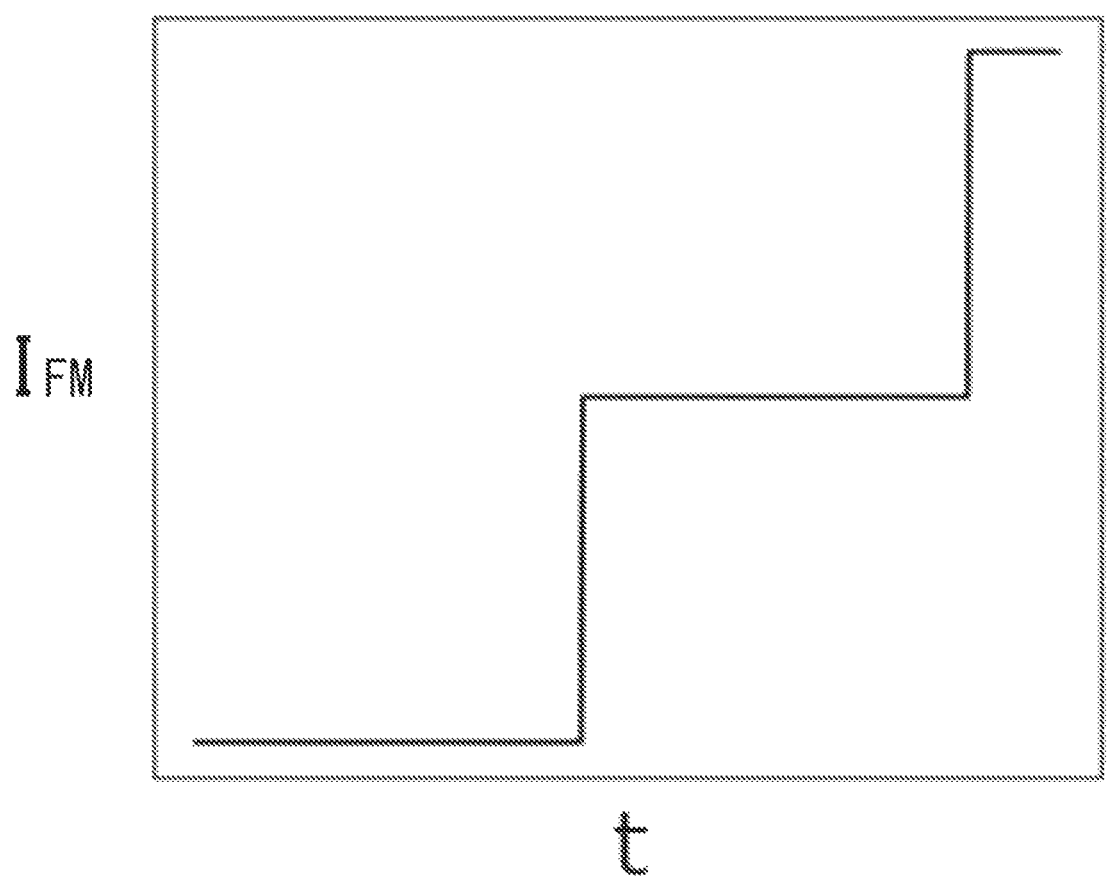
FIG. 10B is a graph illustrating an example in which a current $I_{FM}$ changes with time according to the seventh example embodiment.
Figure 10C:
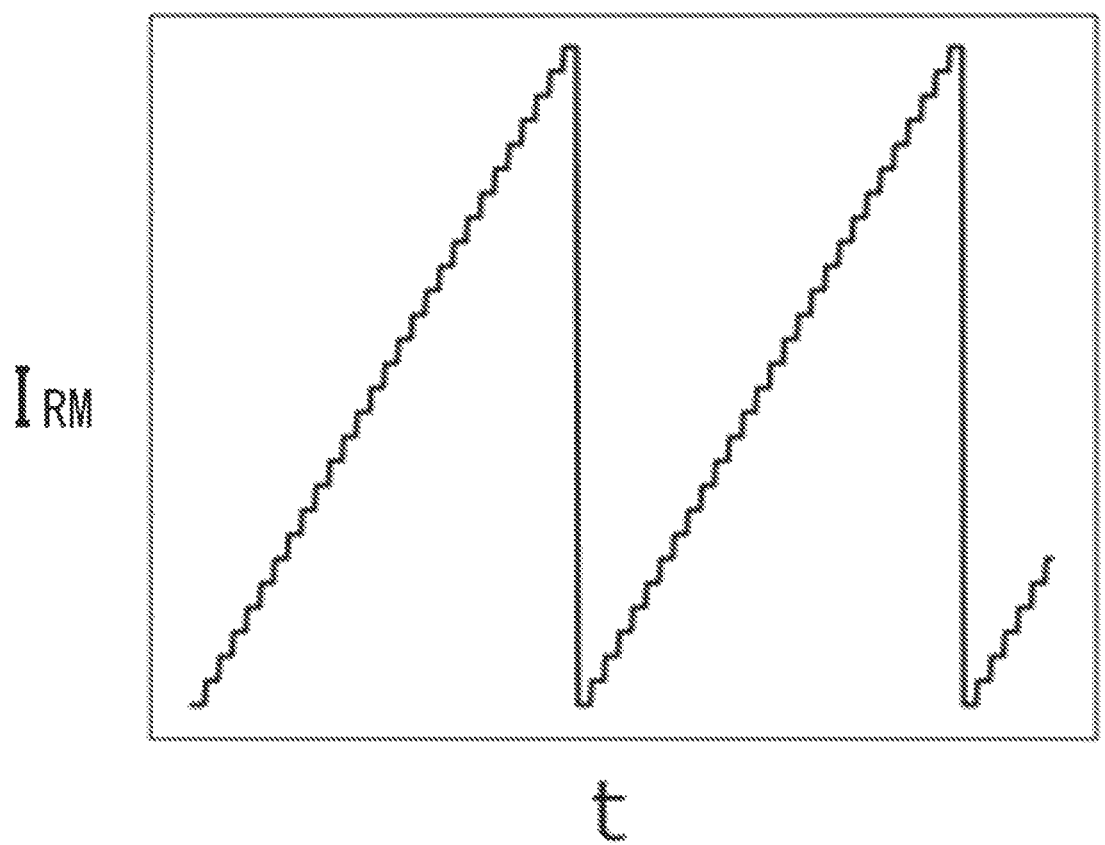
FIG. 10C is a graph illustrating an example in which a current $I_{RM}$ changes with time according to the seventh example embodiment.
Figure 10D:
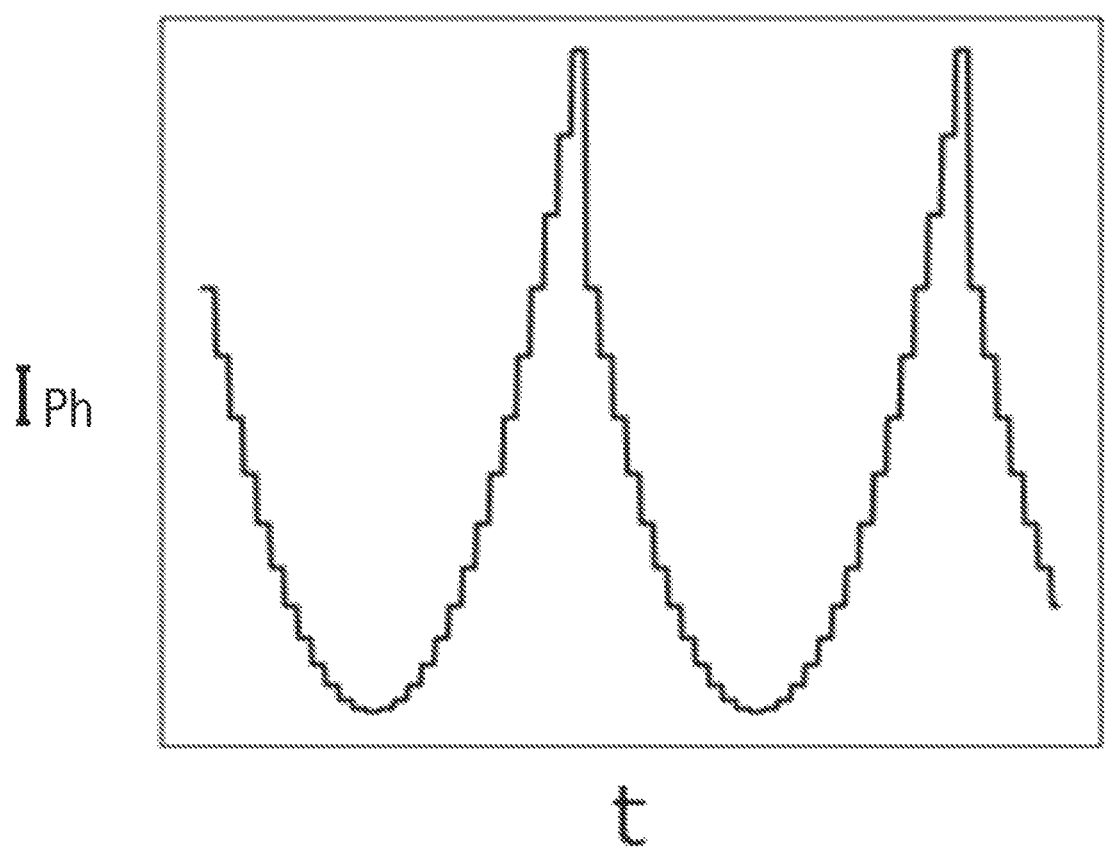
FIG. 10D is a graph illustrating an example in which a current $I_{Ph}$ changes with time according to the seventh example embodiment.

FIGS. 10A to 10E illustrate an example of a change of each of the current $I_G$ 605 to the current $I_{Ph}$ 608 over time. In detail, FIG. 10A illustrates that the current $I_G$ 605 is constant over time, and FIG. 10B illustrates that the current $I_{FM}$ 606 changes with time in a stepped waveform. In addition, FIG. 10C illustrates that the current $I_{RM}$ 607 changes with time in a sawtooth waveform, and FIG. 10D illustrates that the current $I_{Ph}$ 608 changes with time in a shape similar to a sine wave.

Figure 10E:
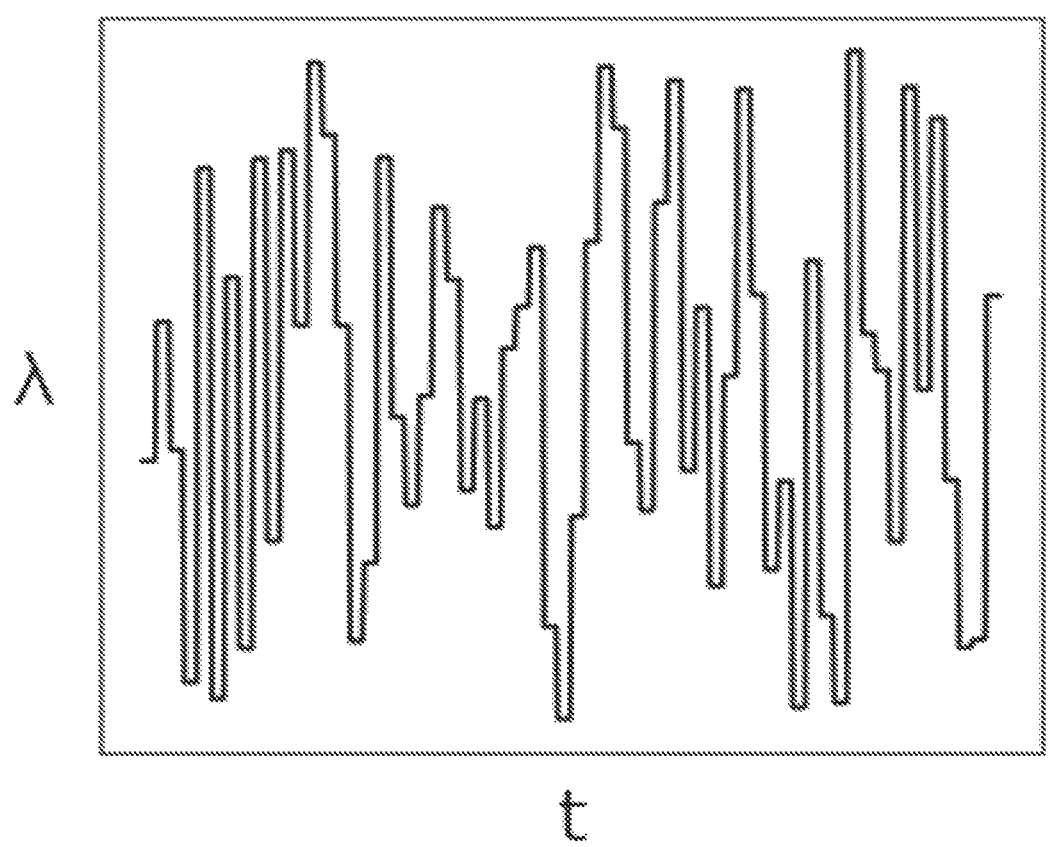
FIG. 10E is a graph illustrating an example in which a wavelength of laser light changes with time according to the seventh example embodiment.

FIG. 10E illustrates an example in which a wavelength λ of the laser light 609 emitted from the SGDBR laser 600 changes with time in a case where each current is tuned as illustrated in FIGS. 10A to 10D. It can be seen from FIG. 10E that the wavelength λ randomly changes with time.

As described above, the wavelength of the laser light of the semiconductor wavelength-tunable laser may be tuned in such a way that the wavelengths of light emitted over a set time interval have the minimum periodicity, and transform matrices sampled at a plurality of wavelengths have the minimum mutual coherence. It can be understood by those skilled in the art that the wavelength of the laser light can be tuned in such a way that the wavelength changes monotonically with time, or may have any number of possible shapes, as long as the individual wavelengths of emitted light constitute a set with the minimum periodicity.

Figure 11:
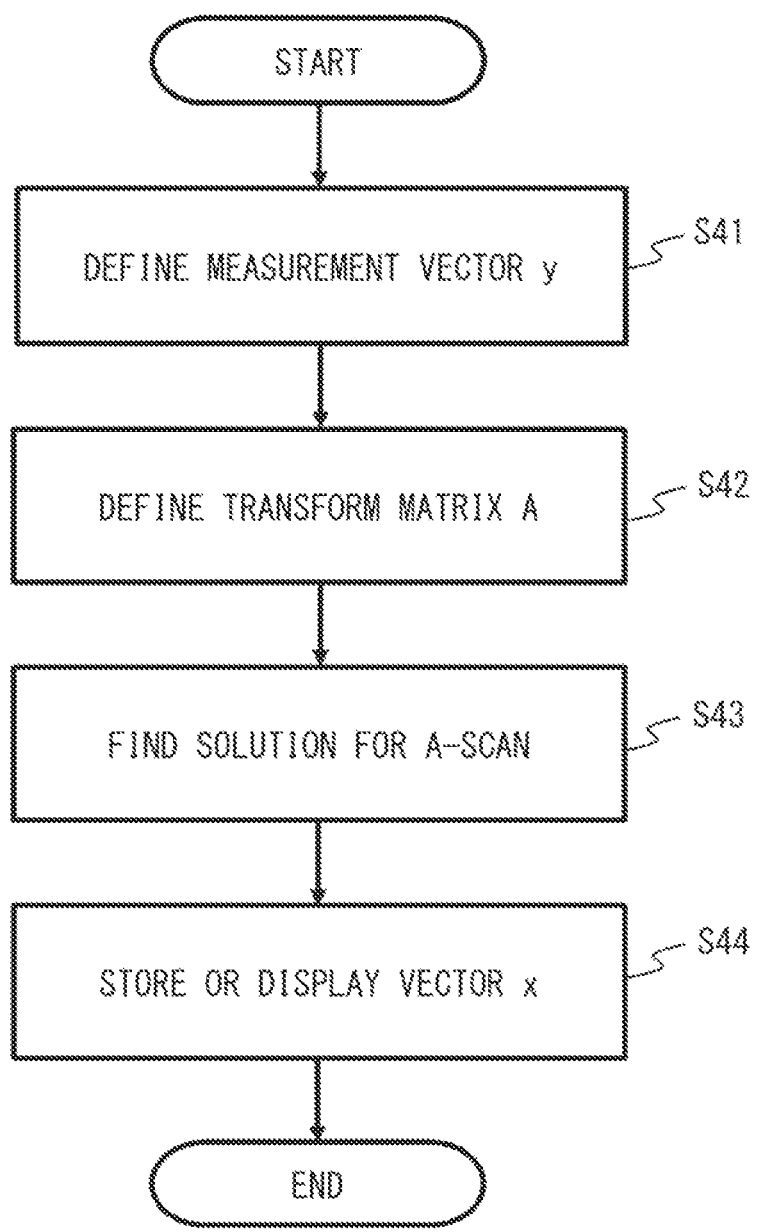
FIG. 11 is a flowchart illustrating an example of a process of using the compressed sensing according to the seventh example embodiment.

FIG. 11 is a flowchart illustrating an example of a process in which the controller 102 uses the compressed sensing to extract an OCT A-scan from a digital interference signal sampled at a set of sample wavelengths.

The controller 102 defines a measurement vector y having, as an element, a measured value of the intensity of a digital interference signal measured at each sample wavelength (step S41). Next, the controller 102 defines a transform matrix A, given by the non-uniform discrete Fourier transform, to transform an OCT A-scan described by the vector x from a sparse depth basis to a measured wavenumber basis (step S42). Specifically, the controller 102 defines the transform matrix A by searching for a pre-calculated matrix from an external or internal memory or a storage device of a processing device, or by calculating the matrix.

The controller 102 finds the solution for the OCT A-scan (that is, the solution representing the scattering profile), for example, by specifying the value of the vector x that minimizes the LASSO described by Formula (5) (step S43). The Lagrange multiplier term λ the LASSO is set in advance or optimized when solving the OCT A-scan.

Finally, the controller 102 executes at least one of processing of storing the vector x representing the OCT A-scan in the memory or the storage device or processing of displaying the vector x on a display unit of the SS-OCT device 100 (step S44).

As described above, the SS-OCT device 100 can suppress a decrease in depth range by using the compressed sensing. Further, since the semiconductor wavelength-tunable laser 103 can be used, the cost of the light source can be reduced.

The plurality of sample wavelengths can be a plurality of wavelengths randomly dispersed within a predetermined wavelength range. As a result, as described above, since the mutual coherence M of the transform matrices is low, it is possible to extract an A-scan having more non-zero elements. Therefore, a situation in which the SS-OCT device 100 is applicable can be expanded.

Furthermore, the SS-OCT device 100 can define the measurement vector, the vector x indicating the scattering profile, and the transform matrix having a row corresponding to each of the plurality of sample wavelengths and a column corresponding to a position in the propagation direction of the measurement light to the sample, and specify a sparse representation of the solution vector by using the measurement vector and the transform matrix. As a result, the SS-OCT device 100 can calculate the solution vector without difficulty.

In addition, various methods can be adopted as a method of specifying the sparse representation of the solution vector. For example, the value of the solution vector may minimize the Lp norm (p is 0 or more and 1 or less) of the solution vector while satisfying the condition that the matrix product of the transform matrix and the solution vector is equal to the measurement vector (Formula (2)). As a result, the compressed sensing technology can be easily applied. In addition, calculation can be facilitated by setting the Lp norm of the solution vector to the L1 norm.

As another method of specifying the sparse representation of the solution vector, a value of the solution vector that minimizes the LASSO may be found. This also enables easy application of the compressed sensing technology.

The measurement device or the SS-OCT device described above can be applied to various applications.

In the example embodiments described above, the disclosure has been described as a hardware configuration, but the disclosure is not limited thereto. The processing (steps) in the device described in each example embodiment of the disclosure described above can also be implemented by causing a processor in a computer to execute a computer program.

Figure 12:
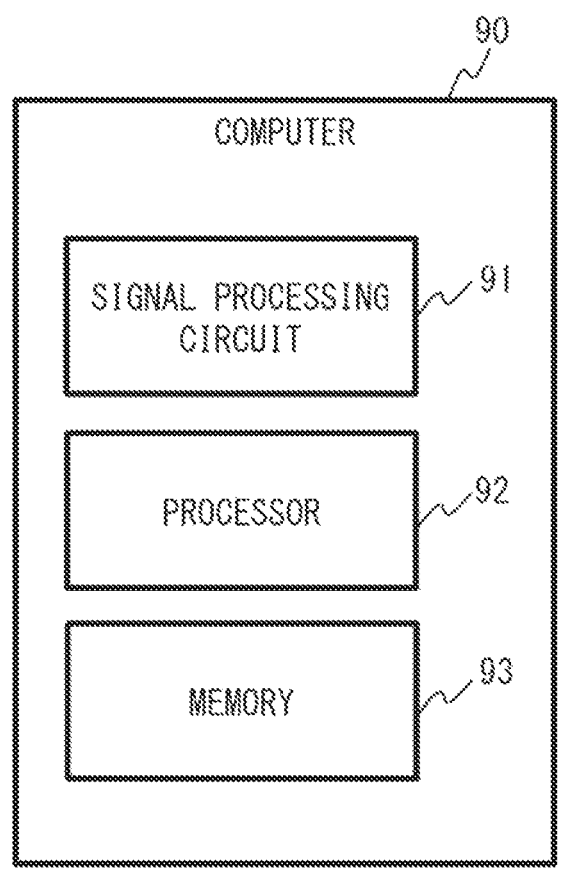
FIG. 12 is a block diagram illustrating an example of a hardware configuration of the device according to each example embodiment.

FIG. 12 is a block diagram illustrating a hardware configuration example of a computer in which the processing of each example embodiment described above is executed. Referring to FIG. 12, a computer 90 includes a signal processing circuit 91, a processor 92, and a memory 93. The computer 90 is, for example, a computer provided in the measurement device 10 and the SS-OCT device 100.

The signal processing circuit 91 is a circuit for processing a signal under the control of the processor 92. The signal processing circuit 91 may include a communication circuit that receives a signal from a transmission device.

The processor 92 reads and executes software (computer program) from the memory 93 to execute the processing in the device described in each example embodiment described above. As an example of the processor 92, one of a central processing unit (CPU), a micro processing unit (MPU), a field-programmable gate array (FPGA), a demand-side platform (DSP), an application specific integrated circuit (ASIC), or a graphics processing unit (GPU) may be used, or a plurality of processors may be used in combination.

The memory 93 includes a volatile memory, a nonvolatile memory, or a combination thereof. The number of memories 93 is not limited to one, and a plurality of memories 93 may be provided. The volatile memory may be, for example, a random access memory (RAM) such as a dynamic random access memory (DRAM) or a static random access memory (SRAM). The nonvolatile memory may be, for example, a random only memory (ROM) such as a programmable random only memory (PROM) or an erasable programmable read only memory (EPROM), or a solid state drive (SSD).

The memory 93 is used to store one or more instructions. Here, one or more instructions are stored in the memory 93 as a software module group. The processor 92 can execute the processing described in the above-described example embodiments by reading and executing these software module groups from the memory 93.

Note that the memory 93 may include a memory built in the processor 92 in addition to a memory provided outside the processor 92. The memory 93 may include a storage disposed away from a processor configuring the processor 92. In this case, the processor 92 can access the memory 93 via an input/output (I/O) interface.

As described above, one or a plurality of processors included in each device in the above-described example embodiments execute one or a plurality of programs including an instruction group for causing a computer to execute an algorithm described with reference to the drawings. With this processing, the signal processing method described in each example embodiment can be implemented.

The program can be stored using various types of non-transitory computer-readable media to be supplied to a computer. The non-transitory computer-readable media include various types of tangible storage media. Examples of the non-transitory computer-readable medium include a magnetic recording medium (for example, a flexible disk, a magnetic tape, or a hard disk drive), an optical magnetic recording medium (for example, a magneto-optical disk), a CD-ROM (Read Only Memory), a CD-R, a CD-R/W, and a semiconductor memory (for example, a mask ROM, a programmable ROM (PROM), an erasable PROM (EPROM), a flash ROM, or a random access memory (RAM). The program may be supplied to the computer by various types of transitory computer-readable media. Examples of transitory computer-readable media include electrical signals, optical signals, and electromagnetic waves. The transitory computer-readable media can supply the programs to the computer via wired communication paths such as wires and optical fiber or wireless communication paths.

Although the disclosure has been described above with reference to the first to seventh example embodiments, the disclosure is not limited to the above. Various modifications that could be understood by those skilled in the art can be made to the configuration and details of the disclosure within the scope of the disclosure.

This application claims priority based on Japanese Patent Application No. 2021-079320 filed on May 7, 2021, and the entire disclosure thereof is incorporated herein.

REFERENCE SIGNS LIST

10 MEASUREMENT DEVICE
11 SEMICONDUCTOR WAVELENGTH-TUNABLE LASER
12 INTERFEROMETER
13 PHOTODETECTOR
14 CONTROL UNIT
100 SS-OCT DEVICE
101 SAMPLE
102 CONTROLLER
103 SEMICONDUCTOR WAVELENGTH-TUNABLE LASER
104 INTERFEROMETER
105 CONTROL SIGNAL
106 LASER LIGHT
107 SAMPLE LIGHT BEAM
108 REFERENCE LIGHT BEAM
109 FIRST OPTICAL INTERFERENCE SIGNAL
110 PHOTODETECTOR
111 ELECTRICAL INTERFERENCE SIGNAL
112 SECOND OPTICAL INTERFERENCE SIGNAL
113 OPTICAL CIRCULATOR
114 INTERMEDIATE FIBER
115 COUPLER
116 SAMPLE OPTICAL FIBER
117 REFERENCE OPTICAL FIBER
118 SAMPLE COLLIMATOR LENS
119 REFERENCE COLLIMATOR LENS
120 REFERENCE MIRROR
121 SCANNER
122 OBJECTIVE LENS
600 SGDBR LASER
601 LASER GAIN MEDIUM
602 FRONT MIRROR
603 REAR MIRROR
604 PHASE SHIFTER DEVICE
605 CURRENT $I_G$
606 Current $I_{FM}$
607 CURRENT $I_{RM}$
608 Current $I_{Ph}$
609 LASER LIGHT

What is claimed is:

1. A measurement method executed by a computer, the measurement method comprising:
   selecting one of a plurality of sample wavelengths as a wavelength of output light of a semiconductor wavelength-tunable laser, and controlling output of the output light in such a way that the selected one sample wavelength discretely and sequentially changes with time;
   acquiring, for each of the plurality of sample wavelengths, an electrical signal obtained by detecting and converting interference light obtained by combining and interfering scattered light obtained by irradiating a sample with measurement light, and reference light for the measurement light and the reference light obtained by splitting the output light; and
   deriving a scattering profile of the sample by performing compressed sensing on the electrical signal obtained for each of the plurality of sample wavelengths,
   wherein in the controlling of the output of the output light, control is performed in such a way that parameters related to the plurality of sample wavelengths satisfy the following Formula (1):

[Mathematical Formula 1]

$$\max_{z=z_0,z_1,\ldots z_n} \hat{f}_{samp}(z) \le \frac{m}{2h-1} \quad (1)$$

(in Formula (1),

[Mathematical Formula 2]

$$\hat{f}_{samp}(z) \quad (2)$$

is a Fourier transform of a sampling mask related to the plurality of sample wavelengths, z is a specific depth at which a depth profile is extracted, m is the number of plurality of sample wavelengths, and h is the number of non-zero elements in a vector of a scattering intensity in a depth range for the scattering profile).

2. The measurement method according to claim 1, wherein the parameters related to the plurality of sample wavelengths satisfy the following Formula (3):

[Mathematical Formula 3]

$$\max_{z=z_0,z_1,\ldots z_n} \hat{f}_{samp}(z) \le \frac{m}{2h-1}, \quad (3)$$

for $$\Delta z < z < z_{max}$$

(in Formula (3), $z_{max}$ is a maximum depth of the scattered light, and $\Delta z$ is a solution of the depth profile).

3. The measurement method according to claim 1, wherein, in the deriving of the scattering profile, the computer performs:
   defining a measurement vector having a measured value of the electrical signal obtained for each of the plurality of sample wavelengths as a constituent element, a solution vector indicating the scattering profile in a propagation direction of the measurement light to the sample, and a non-uniform discrete Fourier transform matrix having a row corresponding to each of the plurality of sample wavelengths and a column corresponding to a position in the propagation direction; and
   specifying a sparse representation of the solution vector by using the measurement vector and the non-uniform discrete Fourier transform matrix.

4. The measurement method according to claim 3, wherein, in the specifying of the sparse representation of the solution vector, the computer performs specifying the sparse representation in such a way that a value of the solution vector minimizes an Lp norm (p is 0 or more and 1 or less) of the solution vector while satisfying a condition that a matrix product of the non-uniform discrete Fourier transform matrix and the solution vector is equal to the measurement vector.

5. The measurement method according to claim 4, wherein the Lp norm of the solution vector is an L1 norm.

6. The measurement method according to claim 3, wherein, in the specifying of the sparse representation of the solution vector, the computer performs specifying the sparse representation by finding a value of the solution vector that minimizes a least absolute shrinkage and selection operator (LASSO).

7. A measurement device comprising:
- a semiconductor wavelength-tunable laser configured to output output light in such a way that a wavelength discretely changes with time;
- an interferometer configured to split the output light into measurement light and reference light and generate interference light obtained by combining and interfering scattered light obtained by irradiating a sample with the measurement light, and the reference light;
- a photodetector configured to detect the interference light and converts the interference light into an electrical signal; and
- a hardware controller configured to select one of a plurality of sample wavelengths as the wavelength of the output light, perform setting in such a way that the selected one sample wavelength sequentially changes with time, and derive a scattering profile of the sample by performing compressed sensing on the electrical signal obtained for each of the plurality of sample wavelengths, wherein the hardware controller controls the semiconductor wavelength-tunable laser to output the output light in such a way that parameters related to the plurality of sample wavelengths satisfy the following Formula (4):

[Mathematical Formula 4]

$$\max_{z=z_0, z_1, \ldots z_n} \hat{f}_{samp}(z) \le \frac{m}{2h-1} \quad (4)$$

(in Formula (4),

[Mathematical Formula 5]

$$\hat{f}_{samp}(z) \quad (5)$$

is a Fourier transform of a sampling mask for the plurality of sample wavelengths, z is a specific depth at which a depth profile is extracted, m is the number of plurality of sample wavelengths, and h is the number of non-zero elements in a vector of a scattering intensity in a depth range for the scattering profile).

8. The measurement device according to claim 7, wherein the semiconductor wavelength-tunable laser is a sampled-grating distributed Bragg reflector (SGDBR) laser.

9. A non-transitory computer-readable medium storing a program for causing a computer to execute:
- selecting one of a plurality of sample wavelengths as a wavelength of output light of a semiconductor wavelength-tunable laser, and controlling output of the output light in such a way that the selected one sample wavelength changes discretely and sequentially with time;
- acquiring, for each of the plurality of sample wavelengths, an electrical signal obtained by detecting and converting interference light obtained by combining and interfering scattered light obtained by irradiating a sample with measurement light, and reference light for the measurement light and the reference light obtained by splitting the output light; and
- deriving a scattering profile of the sample by performing compressed sensing on the electrical signal obtained for each of the plurality of sample wavelengths, wherein in the controlling of the output of the output light, control is performed in such a way that parameters related to the plurality of sample wavelengths satisfy the following Formula (6):

[Mathematical Formula 6]

$$\max_{z=z_0, z_1, \ldots z_n} \hat{f}_{samp}(z) \le \frac{m}{2h-1} \quad (6)$$

(in Formula (6),

[Mathematical Formula 7]

$$\hat{f}_{samp}(z) \quad (7)$$

is a Fourier transform of a sampling mask related to the plurality of sample wavelengths, z is a specific depth at which a depth profile is extracted, m is the number of plurality of sample wavelengths, and h is the number of non-zero elements in a vector of a scattering intensity in a depth range for the scattering profile).

* * * * *